(12) United States Patent
Yamaoka

(10) Patent No.: US 9,164,075 B2
(45) Date of Patent: Oct. 20, 2015

(54) GLUTATHIONE ALKYLESTER ISOTOPOLOGUE AND METHOD FOR DETECTING REACTIVE METABOLITE

(75) Inventor: Toshikazu Yamaoka, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 42 days.

(21) Appl. No.: 14/117,169

(22) PCT Filed: May 21, 2012

(86) PCT No.: PCT/JP2012/003302
§ 371 (c)(1),
(2), (4) Date: Jan. 27, 2014

(87) PCT Pub. No.: WO2012/160798
PCT Pub. Date: Nov. 29, 2012

(65) Prior Publication Data
US 2014/0193847 A1    Jul. 10, 2014

(30) Foreign Application Priority Data

May 20, 2011    (JP) .................................. 2011-113846

(51) Int. Cl.
| C12Q 1/28 | (2006.01) |
| G01N 33/483 | (2006.01) |
| C07B 59/00 | (2006.01) |
| C07K 5/02 | (2006.01) |
| H01J 49/00 | (2006.01) |
| G01N 33/94 | (2006.01) |

(52) U.S. Cl.
CPC ............ G01N 33/4833 (2013.01); C07B 59/00 (2013.01); C07K 5/0215 (2013.01); G01N 33/94 (2013.01); H01J 49/0027 (2013.01); G01N 2458/15 (2013.01)

(58) Field of Classification Search
None
See application file for complete search history.

(56) References Cited

FOREIGN PATENT DOCUMENTS

| JP | 2002-238597 | 8/2002 |
| WO | 2006/012154 | 2/2006 |

OTHER PUBLICATIONS

Defoy et al., Chemical Research in Toxicology, 2011, vol. 24, p. 412-417.*
Ma et al., 2009, Chemico-Biological interactions, vol. 179, p. 25-37.*
International Preliminary Report on Patentability issued Nov. 20, 2013 and English translation of the Written Opinion of the International Searching Authority issued Jul. 17, 2012 in International (PCT) Application No. PCT/JP2012/003302.
International Search Report issued Jul. 17, 2012 in International (PCT) Application No. PCT/JP2012/003302.
Yamada et al., "Idiosyncratic drug toxicity", Folia Pharmacol. Jpn., vol. 127, 2006, pp. 473-480.
Soglia et al., "The development of a higher throughput reactive intermediate screening assay incorporating micro-bore liquid chromatography-micro-electrospray ionization-tandem mass spectrometry and glutathione ethyl ester as an in vitro conjugating agent", Journal of Pharmaceutical and Biomedical Analysis, vol. 36, 2004, pp. 105-116.
Yan et al., "Stable-Isotope Trapping and High-Throughput Screenings of Reactive Metabolites Using the Isotope MS Signature", Analytical Chemistry, vol. 76, No. 23, Dec. 1, 2004, pp. 6835-6847.
Mutlib et al., "Application of stable isotope labeled glutathione and rapid scanning mass spectrometers in detecting and characterizing reactive metabolites", Rapid Communications in Mass Spectrometry, vol. 19, 2005, pp. 3482-3492.
Yan et al., "Use of a Trapping Agent for Simultaneous Capturing and High-Throughput Screening of Both "Soft" and "Hard" Reactive Metabolites", Analytical Chemistry, vol. 79, No. 11, Jun. 1, 2007, pp. 4206-4214.

\* cited by examiner

*Primary Examiner* — Kade Ariani
(74) *Attorney, Agent, or Firm* — Wenderoth, Lind & Ponack, L.L.P.

(57) ABSTRACT

[Problem] To provide a novel isotope-labeled compound that can be used as a trapping agent and that is useful for picking out drug-candidate compounds that produce reactive metabolites.

[Solution] Provided is a glutathione alkylester isotopologue represented by general formula (1). In formula (1), $R^1$ represents a linear or branched alkoxy group in which at least one of carbon, oxygen, and hydrogen atoms contained therein is isotope-labeled and which has 1 to 8 carbon atoms or a cycloalkoxy group in which at least one of carbon, oxygen, and hydrogen atoms contained therein is isotope-labeled and which has 3 to 8 carbon atoms.

7 Claims, 21 Drawing Sheets

GLUTATHIONE ALKYLESTER ISOTOPOLOGUE AND METHOD FOR DETECTING REACTIVE METABOLITE

TECHNICAL FIELD

The present invention relates to a novel isotope-labeled compound and to a method for detecting a reactive metabolite using the isotope-labeled compound as a trapping agent.

BACKGROUND ART

Generally, a pharmaceutical drug is subjected to animal experiments and clinical trials to sufficiently verify its efficacy and safety before approval. However, occasionally, after a pharmaceutical drug is put on the market, it exhibits unidentified fatal drug toxicity such as serious hepatotoxicity and allergic reactions. Such drug toxicity is referred to as idiosyncratic drug toxicity (IDT). At present, it is difficult to predict the occurrence of IDT, but it is considered that a "reactive metabolite" generated by metabolism of the drug is involved in the occurrence of IDT (Non Patent Literature 1). Therefore, it is important for the development of pharmaceutical drugs to devise a scheme for synthesizing drug candidate compounds that do not form reactive metabolites.

One known simple method for examining whether or not a drug candidate compound is metabolized to form a reactive metabolite is a trapping test using a trapping agent. A reactive metabolite is very unstable and is therefore difficult to detect. In the trapping test, the drug candidate compound is incubated in the presence of a metabolic enzyme to examine whether or not a reactive metabolite is formed. In this test, the trapping agent is coexisted with the drug candidate compound. The trapping agent bonds to a reactive metabolite formed from the drug candidate compound through the action of the metabolic enzyme to thereby form an adduct. This trapping agent-reactive metabolite adduct is relatively stable and can be detected using a mass spectrometer etc. Patent Literature 1 discloses glutathione as the trapping agent.

Other reported examples of the compound usable as the trapping agent include glutathione ethyl ester (Non Patent Literature 2). It has been reported that, when glutathione ethyl ester is used as the trapping agent in the analysis using a mass spectrometer, a trapping agent-reactive metabolite adduct can be detected with higher sensitivity than that when glutathione is used as the trapping agent (Non Patent Literature 2).

However, there is a fact that, when the above-described glutathione or glutathione ethyl ester is used as the trapping agent, it is difficult to identify the peak of a trapping agent-reactive metabolite adduct when a liquid chromatography-mass spectrometer (LC-MS) etc. is used to detect the trapping agent-reactive metabolite adduct. Therefore, a peak different from the peak of the trapping agent-reactive metabolite adduct may be misidentified as the peak of the trapping agent-reactive metabolite adduct, and this leads to a misjudgment that a reactive metabolite is formed (a false positive).

One means proposed to prevent a false positive is to use an isotope-labeled compound as a trapping agent. Examples of the isotope-labeled compound usable as the trapping agent include glutathione-glycine-$^{13}C_2,^{15}N$ (Patent Literature 2 and Non Patent Literatures 3 and 4). Glutathione-glycine-$^{13}C_2,^{15}N$ is an isotope-labeled compound in which each of two carbon atoms ($^{12}C$) in the glycine moiety of glutathione is labeled with its isotope ($^{13}C$) and one nitrogen atom ($^{14}N$) in the glycine moiety is labeled with its isotope ($^{15}N$). Glutathione-glycine-$^{13}C_2,^{15}N$ has a mass number larger by 3 than ordinary glutathione. When a mixture of glutathione-glycine-$^{13}C_2,^{15}N$ and ordinary glutathione at a certain ratio (e.g., 1:1) is used as a trapping agent, a glutathione-glycine-$^{13}C_2,^{15}N$-reactive metabolite adduct and a glutathione-reactive metabolite adduct are formed at the above ratio. When an LC-MS, for example, is used to detect these adducts, isotope doublet peaks that differ by 3 in mass number appear. Therefore, the target peaks can be, easily distinguished, so that the possibility of a false positive result can be reduced.

CITATION LIST

Patent Literature

Patent Literature 1: JP2002-238597
Patent Literature 2: WO2006/012154

Non Patent Literature

Non Patent Literature 1: Folia Pharmacol. Jpn. 2006, 127, 473 to 480
Non Patent Literature 2: Journal of Pharmaceutical and Biomedical Analysis, 2004, 36, 105-116
Non Patent Literature 3: Analytical Chemistry, 2004, 76(23), 6835-6847
Non Patent Literature 4: Rapid Communications in Mass Spectrometry, 2005, 19(23), 3482-3492

SUMMARY OF INVENTION

Technical Problem

However, the previously reported isotope-labeled compound usable as the trapping agent is very expensive and not suitable for screening of an enormous number of drug candidate compounds.

It is an object of the present invention to provide a novel isotope-labeled compound that can be used as a trapping agent for identifying a compound that forms a reactive metabolite among drug candidate compounds and to provide a method for detecting a reactive metabolite using the isotope-labeled compound as a trapping agent.

Solution to Problem

The present inventor has conducted extensive studies to achieve the above object and found a glutathione alkyl ester isotopologue represented by general formula (1) (hereinafter also referred to as a substitution product represented by general formula (1)). The substitution product represented by general formula (1) can be easily prepared from glutathione which is available at low price.

[Chemical Formula 1]

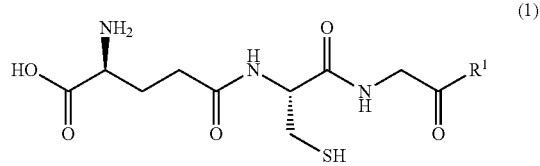

In formula (1), $R^1$ represents a linear or branched alkoxy group in which at least one of carbon, oxygen, and hydrogen atoms contained therein is isotope-labeled and which has 1 to 8 carbon atoms or a cycloalkoxy group in which at least one of carbon, oxygen, and hydrogen atoms contained therein is isotope-labeled and which has 3 to 8 carbon atoms.

The substitution product represented by general formula (1) includes an isotope in its structure. Therefore, when the substitution product represented by general formula (1) is used as a trapping agent to detect a reactive metabolite, the same principle as that for conventional isotopic trapping agents (such as glutathione-glycine-$^{13}C_2$,$^{15}N$) can be applied, and ion peaks originating from trapping agent-reactive metabolite adducts can be easily identified in LC-MS analysis etc. This allows detection with less false positive results.

To detect a reactive metabolite, LC-MS analysis, for example, is performed. The present inventor has found that ion peaks originating from trapping agent-reactive metabolite adducts can be more easily detected by using, in the LC-MS analysis, a measurement method, such as a full scan method or a neutral loss scan method, which can detect ions continuously over a wide range. This allows detection with less false negative results.

Accordingly, the present invention includes the following inventions.

[1] A glutathione alkyl ester isotopologue represented by general formula (1).

[Chemical Formula 2]

(1)

In formula (1), $R^1$ represents a linear or branched alkoxy group in which at least one of carbon, oxygen, and hydrogen atoms contained therein is isotope-labeled and which has 1 to 8 carbon atoms or a cycloalkoxy group in which at least one of carbon, oxygen, and hydrogen atoms contained therein is isotope-labeled and which has 3 to 8 carbon atoms.

[2] The glutathione alkyl ester isotopologue according to [1], wherein the glutathione alkyl ester isotopologue is represented by general formula (2), and at least one of carbon, oxygen, and hydrogen atoms marked with an asterisk is isotope-labeled.

[Chemical Formula 3]

(2)

[3] The glutathione alkyl ester isotopologue according to [1], wherein the glutathione alkyl ester isotopologue is represented by general formula (3).

[Chemical Formula 4]

(3)

In formula (3), D represents deuterium ($^2H$).

[4] A method for detecting a reactive metabolite comprising using the glutathione alkyl ester isotopologue according to any one of [1] to [3].

[5] The method for detecting a reactive metabolite according to [4], comprising:

incubating a reaction sample containing the glutathione alkyl ester isotopologue according to any one of [1] to [3], an auxiliary detection compound which is a compound obtained by substituting at least one atom contained in the glutathione alkyl ester isotopologue with an atom having a mass number different from a mass number of the at least one atom, and a drug candidate compound in the presence of a drug metabolic enzyme to thereby form a product containing a glutathione alkyl ester isotopologue-reactive metabolite adduct and an auxiliary detection compound-reactive metabolite adduct; and detecting a mass peak of the formed glutathione alkyl ester isotopologue-reactive metabolite adduct and a mass peak of the formed auxiliary detection compound-reactive metabolite adduct through analysis using a liquid chromatography-mass spectrometer (LC-MS).

[6] The method for detecting a reactive metabolite according to [5], wherein a molar ratio of the glutathione alkyl ester isotopologue according to anyone of [1] to [3] to the auxiliary detection compound in the reaction sample is 2:1 to 1:2.

[7] The method for detecting a reactive metabolite according to [5] or [6], the method further comprising:

adding dithiothreitol, 2-mercaptoethanol, or tris(2-carboxyethyl)phosphine to the product obtained by incubation; and then performing the analysis using the liquid chromatography-mass spectrometer (LC-MS).

[8] The method for detecting a reactive metabolite according to any one of [5] to [7], wherein a neutral loss scan method or a full scan method is performed in the analysis using the liquid chromatography-mass spectrometer (LC-MS).

[9] The method for detecting a reactive metabolite according to any one of [5] to [8], wherein the auxiliary detection compound is a non-labeled compound of the glutathione alkyl ester isotopologue according to any one of [1] to [3] contained in the reaction sample.

[10] A method for producing a glutathione alkyl ester isotopologue according to any one of [1] to [3], comprising reacting glutathione with a deuterated alcohol.

[11] The method for producing the glutathione alkyl ester isotopologue according to [10], wherein the deuterated alcohol is ethanol-d6.

Advantageous Effects of Invention

The substitution product represented by general formula (1) has been found as an isotope-labeled compound usable as a novel trapping agent. The substitution product represented by general formula (1) can be prepared at much lower cost as compared to conventional isotope-labeled compounds used as a trapping agent. Therefore, screening of an enormous number of drug candidate compounds, which has conventionally been difficult to achieve, can be achieved.

DESCRIPTION OF EMBODIMENTS

Figure 1:
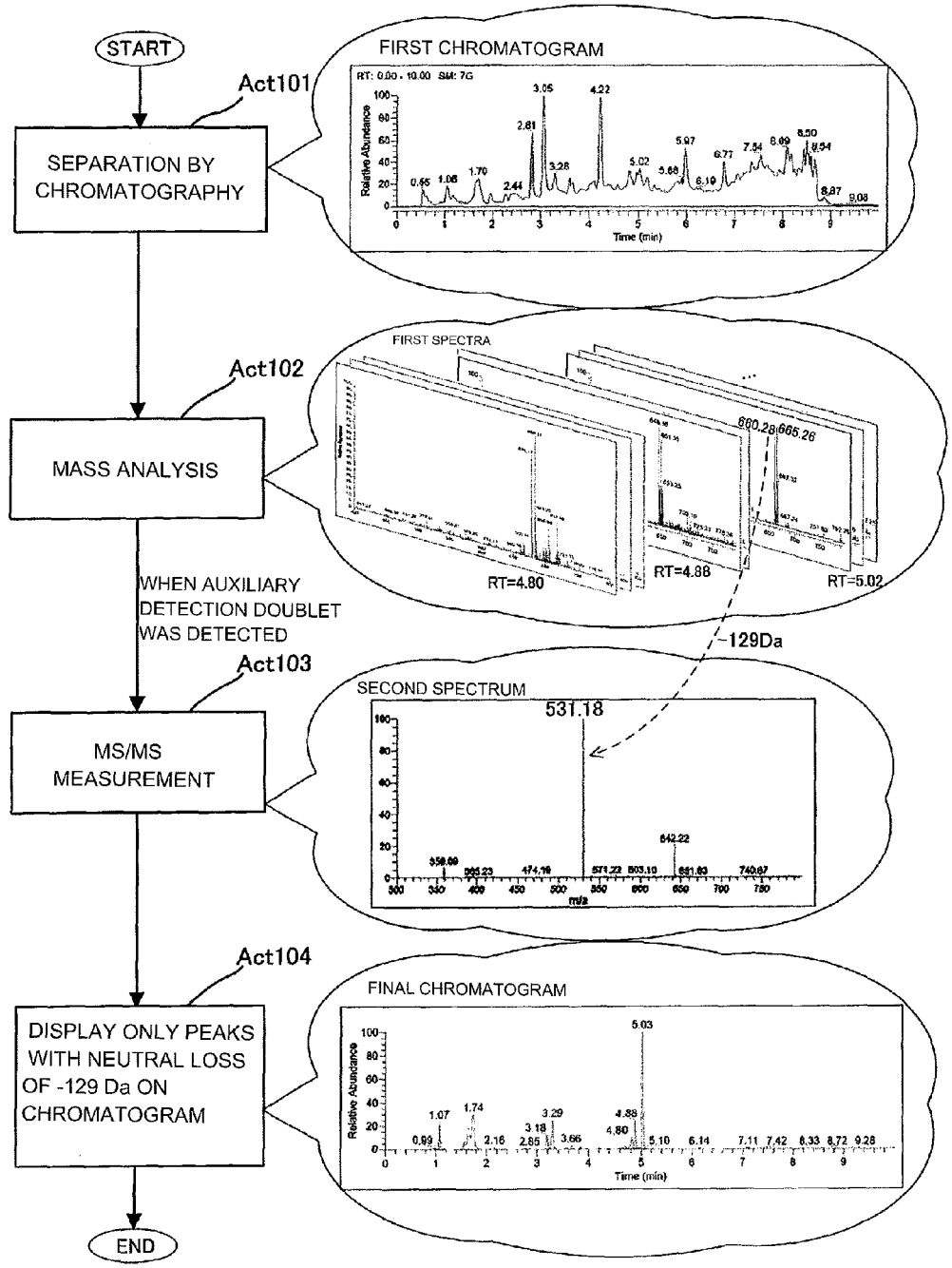
FIG. 1 is a diagram illustrating an example of a process flow of LC-MS analysis of a reactive metabolite.

One embodiment of the present invention will next be described in detail.

In this embodiment, the substitution product represented by general formula (1), which is an isotope-labeled compound, is used to detect a reactive metabolite.

[Chemical Formula 5]

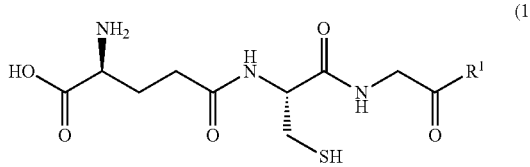

(1)

In formula (1), $R^1$ represents a linear or branched alkoxy group in which at least one of carbon, oxygen, and hydrogen atoms contained therein is isotope-labeled and which has 1 to 8 carbon atoms or a cycloalkoxy group in which at least one of carbon, oxygen, and hydrogen atoms contained therein is isotope-labeled and which has 3 to 8 carbon atoms.

In the following description, a description of the definition of a functional group included in a general formula may be omitted, and the definition already described may be quoted instead.

The term "isotope-labeled compound" as used herein refers to a compound in which at least one atom contained therein is substituted with its isotope. The term "isotope" as used herein refers to an atom having the same atomic number as that of atoms dominant in nature but having a mass number (neutron number) different from the mass number of the atoms dominant in nature.

The term "drug candidate compound" as used herein refers to a compound subjected to various tests for the purpose of development of pharmaceutical drugs, and the drug candidate compound is not limited to a compound that forms a reactive metabolite.

The term "reactive metabolite" as used herein means an electrophilic or radical compound formed when a substrate compound is metabolized by a drug metabolic enzyme described later to change its chemical structure. Among such reactive metabolites, the electrophilic compound has, in its molecule, an electrophilic functional group such as an epoxide group, a quinone group, an unsaturated carbonyl group, or an imine group. Among the reactive metabolites, the radical compound has a highly reactive free radical in its molecule.

The term "drug metabolic enzyme" as used herein refers to any enzyme that is derived from human or animal tissue and can metabolize a drug candidate compound. The drug metabolic enzyme used to detect a reactive metabolite is preferably an enzyme derived from human or rat tissue and more preferably an enzyme derived from human tissue. Particularly, an enzyme derived from liver tissue is preferred. Examples of the drug metabolic enzyme include a cytochrome P450 enzyme, peroxidase, cyclooxygenase, and myeloperoxidase.

The drug metabolic enzyme may be used in an isolated form or may be used in a form in which the drug metabolic enzyme is contained in cells or cell fractions, and a person skilled in the art may be appropriately set the form of the drug metabolic enzyme.

The phrase "a form in which the drug metabolic enzyme is contained in cells or cell fractions" as used herein means cells or cell fractions derived from human or animal tissue in which the "drug metabolic enzyme" is contained. Examples of the cells or cell fractions containing the drug metabolic enzyme include cells, S9 fractions, microsomal fractions, and soluble fractions. Any of cells, S9 fractions, and microsomal fractions may be preferably used. More preferably, any of liver cells, liver S9, and liver microsomes may be used.

The drug metabolic enzyme may be used in combination with a coenzyme to detect a reactive metabolite. Examples of the coenzyme include: oxidized coenzymes such as oxidized nicotinamide adenine dinucleotide (NAD+) and oxidized nicotinamide adenine dinucleotide phosphate (NADP+); and reduced coenzymes such as reduced nicotinamide adenine dinucleotide (NADH) and reduced nicotinamide adenine dinucleotide phosphate (NADPH). Preferably, NADPH or NADP+ is used in combination with the drug metabolic enzyme.

In a preferred form, a combination of liver cells, liver S9, or liver microsomes with a coenzyme, NADPH or NADP+, is used to detect a reactive metabolite. Of these, a combination of liver microsomes and NADPH is more preferred.

The term "liquid chromatography-mass spectrometer (LC-MS)" as used herein refers to a system including a liquid chromatography and a mass spectrometer connected thereto. In this system, first, a plurality of compounds contained in a measurement sample are separated using the liquid chromatograph (LC). Then the obtained LC eluate is successively introduced into the mass spectrometer (MS) and ionized, and the ions are detected. Since ions (parent ions) originating from the compounds contained in the LC solution are generated, the presence of the compounds can be determined by detecting the mass-to-charge ratios (m/z) of the ions. In this case, an appropriate scan method may be selected.

The mass-to-charge ratio (m/z) is a value obtained by mass analysis and is a value obtained by dividing the mass (m) of an ion obtained by ionization of a molecule in the measurement sample by the charge number (z) of the ion. The mass of the molecule can be determined from the mass-to-charge ratio (m/z) of the ion and its charge number (z).

The term "MS/MS measurement" as used herein refers to a method for detecting ions (daughter ions) generated by activating arbitrarily selected parent ions obtained in the MS measurement through collision with an inert gas. An appropriate scan method may be used to measure the mass-to-charge ratios (m/z) of the daughter ions. Examples of the inert gas include helium and argon.

Examples of the liquid chromatography (LC) include a high-performance liquid chromatograph (HPLC), an ultra performance LC (UPLC), and an ultra fast LC (UFLC). Of these, an UPLC is preferred.

Examples of the mass spectrometer (MS) include a quadrupole mass spectrometer, an ion trap mass spectrometer, a time-of-flight mass spectrometer, a magnetic field mass spectrometer, and a Fourier transform ion cyclotron resonance mass spectrometer (FT-ICR).

Examples of the ionization method usable in the mass spectrometer (MS) include an electrospray ionization (ESI) method and an atmospheric pressure chemical ionization (APCI) method. Of these, ESI is preferred.

Examples of the scan method used in the mass spectrometer (MS) include a full scan method, a neutral loss scan method, an SRM method, and a product ion scan method. Of these, a neutral loss scan method or a full scan method is used preferably because false negative results can be reduced.

The full scan method is a method in which parent ions are continuously detected in an arbitrarily selectable mass-to-charge ratio (m/z) range. In this method, since measurement is performed over the entire width of a mass range (an arbitrarily selectable mass range having a certain width), all trapping agent-reactive metabolite adducts formed can be detected.

The neutral loss scan method is a method in which parent ions are continuously detected in an arbitrarily selectable mass-to-charge ratio (m/z) range. In this method, parent ions from which a neutral molecule having a specific mass number has been separated are detected.

The SRM method is a method in which daughter ions having a specific mass-to-charge ratio (m/z) are generated from parent ions having a specific mass-to-charge ratio (m/z) and both the ions (parent ions and daughter ions) are detected. This method is a measurement method in which the structure of a trapping agent-reactive metabolite adduct generated from a drug candidate compound and a trapping agent is predicted and the measurement range is narrowed on the basis of the mass of the trapping agent-reactive metabolite adduct. Since detection is performed in a specific range, the influence of impurities is small, and high sensitivity measurement can be achieved.

The product ion scan method is a method in which daughter ions generated from parent ions having a specific mass-to-charge ratio (m/z) are continuously detected in an arbitrarily selectable mass-to-charge ratio (m/z) range.

When an unpredictable reactive metabolite is formed, the ions thereof may not be detected when the SRM method is used. However, the use of the full scan method allows comprehensive detection. In the development of pharmaceutical drugs, the capability of capturing unpredictable reactive metabolites is useful, and this is important information that contributes to subsequent drug candidate compound designs.

The term "chromatogram" as used herein refers to a graph of the results of MS measurement for an LC eluate, with the horizontal axis representing retention time and the vertical axis representing relative abundance.

The term "mass spectrum" as used herein refers to a graph of the results of MS measurement at an arbitrary time, with the horizontal axis representing mass-to-charge ratio (m/z) and the vertical axis representing relative abundance.

The phrase "at least one of carbon, oxygen, and hydrogen atoms is isotope-labeled" means that at least one of carbon, oxygen, and hydrogen atoms is substituted with its isotope.

Examples of the isotope of a carbon atom include $^{13}C$ and $^{14}C$. Examples of the isotope of an oxygen atom include $^{18}O$. Examples of the isotope of a hydrogen atom include $^{2}H$ (also represented as D) and $^{3}H$.

Examples of the "linear or branched alkoxy group which has 1 to 8 carbon atoms" include a methoxy group, an ethoxy group, a 1-methylethoxy group, a 1,1-dimethylethoxy group, a 1-propoxy group, a 2-propoxy group, a 2-methyl-2-propoxy group, a 1-ethylpropoxy group, a 2-ethylpropoxy group, a 1-butoxy group, a 2,3-dimethyl-2-butane-2-oxy group, a 2,3-dimethylbutane-2-oxy group, a 1-pentoxy group, a 1-hexyloxy group, a 1-heptyloxy group, and a 1-octyloxy group.

Examples of the "cycloalkoxy group which has 3 to 8 carbon atoms" include a cyclopropoxy group, a cyclopropylmethoxy group, a cyclobutoxy group, a cyclopentoxy group, a cyclohexyloxy group, a cycloheptyloxy group, and a cyclooctyloxy group.

The term "auxiliary detection compound" as used herein refers to a compound mixed with a reaction sample and used to detect a reactive metabolite. The auxiliary detection compound is a compound in which at least one atom contained in the glutathione alkyl ester isotopologue in this embodiment used as the trapping agent is substituted with an atom having a mass number (neutron number) different from that of the at least one atom. Therefore, the auxiliary detection compound has the same skeleton as that of the glutathione alkyl ester isotopologue in this embodiment used as the trapping agent, and the same functional group (atom) as that in the glutathione alkyl ester isotopologue is bonded at the same position with the same configuration as those in the glutathione alkyl ester isotopologue. The glutathione alkyl ester isotopologue in this embodiment used as the trapping agent and the auxiliary detection compound are different at least one of the mass number (neutron number) of atoms, and therefore these compounds differ only in molecular weight.

A person skilled in the art may be appropriately set the molecular weight of the auxiliary detection compound in consideration of the ease of identification in the mass analysis etc.

The auxiliary detection compound bonds to a reactive metabolite, as does the glutathione alkyl ester isotopologue in this embodiment. Therefore, the auxiliary detection compound may be considered as a trapping agent for detecting a reactive metabolite.

For example, a non-labeled compound of the substitution product represented by general formula (1) that is mixed with a reaction sample may be used as the auxiliary detection compound. The non-labeled compound means a compound in which all the isotope atoms contained in the glutathione alkyl ester isotopologue are substituted with non-isotopic atoms.

More specifically, when the glutathione alkyl ester isotopologue contains a carbon isotope $^{13}C$, the non-labeled compound of this glutathione alkyl ester isotopologue is a compound in which the $^{13}C$ is substituted with $^{12}C$. Similarly, when the glutathione alkyl ester isotopologue contains an oxygen isotope $^{18}O$, the non-labeled compound of this glutathione alkyl ester isotopologue is a compound in which the $^{18}O$ is substituted with $^{16}O$. When the glutathione alkyl ester isotopologue contains a hydrogen isotope $^{2}H$, the non-labeled compound of this glutathione alkyl ester isotopologue means a compound having a structure in which the $^{2}H$ is substituted with $^{1}H$.

The term "trapping agent" as used herein refers to a compound used to detect a reactive metabolite and covalently bonds to the reactive metabolite to form a covalent complex more stable than the reactive metabolite (this complex is referred to as a trapping agent-reactive metabolite adduct).

The term "auxiliary detection compound-reactive metabolite adduct" as used herein means a covalent complex of the auxiliary detection compound and a reactive metabolite.

The term "glutathione alkyl ester isotopologue-reactive metabolite adduct" as used herein means a covalent complex of a reactive metabolite and the glutathione alkyl ester isotopologue, which is the isotope-labeled compound in this embodiment.

When analysis using the LC-MS is performed on a mixture of an auxiliary detection compound-reactive metabolite adduct and a glutathione alkyl ester isotopologue-reactive metabolite adduct, mass peaks with different mass-to-charge ratios (m/z) corresponding to the difference in mass between the glutathione alkyl ester isotopologue and the auxiliary detection compound (e.g., two mass peaks, a doublet) are detected. In the present specification, this doublet is referred to as an auxiliary detection doublet. Among auxiliary detection doublets, a doublet that appears when the non-labeled compound of the glutathione alkyl ester isotopologue is used as the auxiliary detection compound is referred to as "an isotopic doublet."

The term "false positive" as used herein means that results (positive results) showing the formation of a reactive metabolite are obtained although no reactive metabolite has been actually formed during incubation of a drug candidate compound and a drug metabolic enzyme. Such a false positive is not preferred because a safe compound that does not form a reactive metabolite is excluded from the candidates for pharmaceutical drugs.

The term "false negative" as used herein means that results (negative results) showing no formation of a reactive metabolite are obtained although a reactive metabolite has been actually formed during incubation of a drug candidate compound and a drug metabolic enzyme. Such a false negative is not preferred because a compound that forms a reactive metabolite is misidentified as a safe compound.

(Example of Detection of Reactive Metabolite)

An example of detection of a reactive metabolite will be described.

(Step 1) In-Vitro Incubation and Sample Preparation

The substitution product represented by general formula (1), an auxiliary detection compound, and a drug candidate compound are mixed to prepare a reaction sample. No particular limitation is imposed on the ratio of the substitution product represented by general formula (1) to the auxiliary detection compound, and a person skilled in the art may be appropriately set the ratio. The ratio by mole is preferably 2:1 to 1:2 and more preferably 1:1. The reaction sample is incubated in the presence of a drug metabolic enzyme. No particular limitation is imposed on the conditions for incubation. For example, a person skilled in the art may be appropriately set the concentration of the drug metabolic enzyme, the concentration of the drug candidate compound, etc. according to the desired sensitivity in LC-MS analysis in step 2 described later. The drug metabolic enzyme in microsomal fractions etc. may be mixed into the reaction sample as described above. Therefore, the concentration of the drug metabolic enzyme can be controlled on the basis of the concentration of protein in the reaction sample. The reaction time and reaction temperature may be appropriately set according to the desired sensitivity in the LC-MS analysis and may be, for example, 37° C. and 60 minutes.

The drug metabolic enzyme present in the reaction sample may be in the form in which it is contained in cells or cell fractions. A coenzyme such as NADPH may be added to the reaction sample. After incubation, analysis is performed using the LC-MS.

The substitution product represented by general formula (1) in this embodiment sometimes forms a disulfide bond at the position of the thiol group, and a dimerized product is thereby formed. In such a case, the disulfide bond can be reduced by adding dithiothreitol (DTT) to the product obtained by incubation before the LC-MS analysis. The appearance of a large peak of the dimerized product in a chromatogram in the LC-MS analysis can thereby be suppressed, so that the peak of a trapping agent-reactive metabolite adduct can be easily identified. Instead of dithiothreitol, a reducing agent such as 2-mercaptoethanol or tris(2-carboxyethyl)phosphine may be used.

(Step 2) LC-MS Analysis

A schematic diagram of an example of the LC-MS analysis is shown in FIG. 1. Four types of device data charts shown in FIG. 1 are referred to, from top to bottom, as a first chromatogram, a first spectrum, a second spectrum, and a final chromatogram.

The first chromatogram is a chart showing the results of mass analysis performed by successively introducing the LC eluate of compounds separated by liquid chromatography (LC) into the mass spectrometer (MS). In the first chromatogram, the horizontal axis represents retention time of compounds corresponding to respective peaks in the column used in the liquid chromatography (hereinafter simply referred to as retention time), and the vertical axis represents the relative abundance of ions for each peak.

The first spectrum is a chart showing the results of mass analysis at a specific time in the first chromatogram. In the first spectrum, the horizontal axis represents mass-to-charge ratio (m/z), and the vertical axis represents the relative abundance of ions for each peak.

The second spectrum is a chart showing the results of MS/MS measurement. In the second spectrum, the horizontal axis represents mass-to-charge ratio (m/z), and the vertical axis represents the relative abundance of ions for each peak.

The final chromatogram is a chart in which, only the peaks with a specified neutral loss of mass detected in the MS/MS measurement among the peaks appearing in the first chromatogram are shown as a chromatogram. In the final chromatogram, the horizontal axis represents retention time, and the vertical axis represents the relative abundance of ions for each peak.

As shown in FIG. 1, the sample prepared in step 1 (the product obtained by incubation) is subjected to liquid chromatography (LC) for separation, and the obtained LC eluate is introduced into the mass spectrometer (MS). In the MS, after ionization, mass analysis is performed to obtain a first chromatogram and first spectra (Act101 and Act102).

The measurement range in the mass analysis is preferably a range in which the mass-to-charge ratio (m/z) of an adduct formed from the object compound and the trapping agent can be detected. Preferably, full scan measurement is performed under the conditions in which the selected range of mass-to-charge ratio (m/z) is, for example, 350 to 1,200.

The presence or absence of an auxiliary detection doublet in each of the obtained first spectra is checked. To check the presence of the doublet, the data of the first spectrum may be visually analyzed, or MS pattern recognition (the difference in mass between the substitution product of general formula (1) and the auxiliary detection Compound and their intensities are defined, and ions that meet these conditions are mechanically detected) may be used.

When an auxiliary detection doublet is observed in a first spectrum, MS/MS measurement may be performed (Act103). In the MS/MS measurement performed when the auxiliary detection doublet is observed, MS/MS fragments are checked. This can further reduce the possibility of a false positive result.

It is known that a pyroglutamic acid molecule having a mass number of 129 Da is separated from a compound having a glutathione alkyl ester structure by collisional activation. Preferably, in the MS/MS measurement, collisional activation is performed under energy settings that allow a neutral loss of 129 Da to be detected.

A second spectrum is obtained from the results of the MS/MS measurement. A preferred range of energy settings is a normalized collision energy range of 5 to 50.

In the MS/MS measurement performed after collisional activation, detection with less false positive results can be more effectively performed by subjecting, to the measurement, only ions corresponding to peaks identified as the auxiliary detection doublet with an intensity ratio the same as the mixing ratio of the substitution product represented by general formula (1) to the auxiliary detection compound (the mixing ratio is preferably 2:1 to 1:2 and more preferably 1:1). Therefore, it is preferable to use an isotopic data dependent scan mode.

The "isotopic data dependent scan mode" is a mode in which MS/MS measurement is performed only when ions with a pre-specified mass difference and a pre-specified intensity ratio are detected during full scan measurement.

After the MS/MS measurement, the obtained data set may be subjected to a 129 Da neutral loss filter (Act104).

The "neutral loss filter" is a data analysis method in which only data with a specified neutral loss of mass in the obtained data is displayed as a chromatogram. A final chromatogram is obtained through the use of the neutral loss filter (see FIG. 1). The obtained final chromatogram allows the peaks specific to the formed trapping agent-reactive metabolite adducts to be identified more easily.

(Example of Production Method)

An example of the method for producing the substitution product represented by general formula (1) is shown in Scheme 1.

Scheme 1

[Chemical Formula 6]

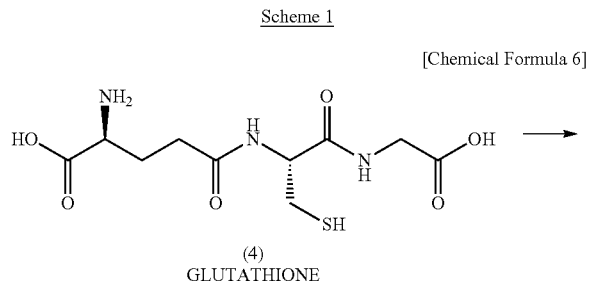

(4)
GLUTATHIONE

-continued

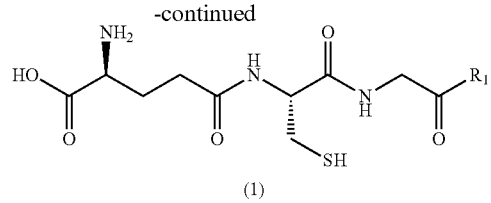

(1)

In formula (1), $R^1$ represents a linear or branched alkoxy group in which at least one of carbon, oxygen, and hydrogen atoms is isotope-labeled and which has 1 to 8 carbon atoms or a cycloalkoxy group in which at least one of carbon, oxygen, and hydrogen atoms is isotope-labeled and which has 3 to 8 carbon atoms.

The glutathione alkyl ester isotopologue represented by general formula (1) can be derived and produced from, for example, glutathione represented by general formula (4).

For example, the glutathione alkyl ester isotopologue can be produced by reacting glutathione represented by formula (4) with an alcohol represented by general formula (5) containing an isotope in the presence of a catalyst.

[Chemical Formula 7]

$$H''\text{—}R' \quad (5)$$

In general formula (5), $R^1$ is as described above, and the hydrogen atom marked with two asterisks may also be substituted with an isotope.

More specifically, glutathione represented by formula (4) is reacted with isotope-labeled ethanol represented by general formula (6) in the presence of a catalyst. A glutathione alkyl ester isotopologue represented by general formula (2) can thereby be obtained.

[Chemical Formula 8]

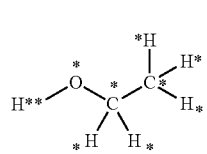

(6)

In general formula (6), at least one of carbon, oxygen, and hydrogen atoms marked with an asterisk is isotope-labeled. In general formula (6), the hydrogen atom marked with two asterisks may also be substituted with an isotope.

[Chemical Formula 9]

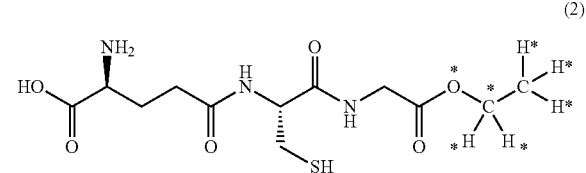

(2)

In general formula (2), at least one of carbon, oxygen, and hydrogen atoms marked with an asterisk is isotope-labeled.

Examples of the alcohol represented by general formula (5) and containing an isotope include methanol-d3, methanol-d4, ethanol-1,1-d2, ethanol-2,2,2-d3, ethanol-d5, ethanol-d6, propanol-1,1-d2, propanol-2,2-d2, propanol-3,3,3- d3, propanol-d7, propanol-d8, isopropanol-1,1,1,3,3,3-d6, isopropanol-d8, butanol-d10, 1-pentanol-d11, cyclohexanol-d12, and octanol-d18. The alcohol is preferably ethanol-1,1-d2, ethanol-2,2,2-d3, ethanol-d5, or ethanol-d6 and is more preferably ethanol-d6.

The catalyst is used in an amount of 0.5 to 10 equivalents to glutathione, preferably 1 to 2 equivalents, and more preferably 1.6 equivalents.

The reaction temperature may be in the range of 0° C. to the boiling point of the alcohol containing an isotope and is preferably 20° C. to 40° C. and more preferably 25° C. to 35° C.

(Comparison with Conventional Technique)

In the conventional isotope-labeled compound used as a trapping agent, isotopes are present in a glycine residue, which is a constituent amino acid of glutathione (Patent Literature 2 and Non Patent Literatures 3 and 4). The present inventor has made it possible to provide a low-cost isotope-labeled compound that can be used as a trapping agent by isotope-labeling an element included in $R^1$, which is not a constituent amino acid moiety of glutathione.

[Chemical Formula 10]

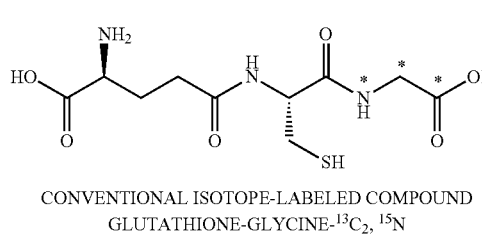

(7)

CONVENTIONAL ISOTOPE-LABELED COMPOUND
GLUTATHIONE-GLYCINE-$^{13}C_2$, $^{15}N$

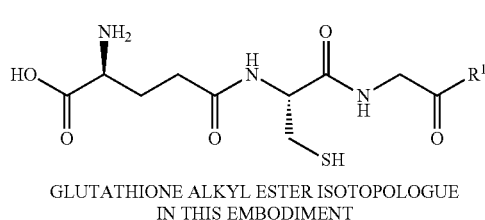

(1)

GLUTATHIONE ALKYL ESTER ISOTOPOLOGUE
IN THIS EMBODIMENT

In formula (7), atoms marked with an asterisk are $^{13}C$ or $^{15}N$. In formula (1), $R^1$ is as described above.

Glutathione which is available at low price can be used as a synthetic raw material of the substitution product represented by general formula (1). For example, the substitution product represented by general formula (1) can be easily prepared in one step at high yield by reacting commercial glutathione with an isotope-containing alcohol (the alcohol represented by general formula (5)) such as commercial deuterated ethanol.

On the other hand, although glutathione-glycine-$^{13}C_2$,$^{15}N$ in the conventional technology is commercially available, it is a very expensive reagent, so that it is difficult to purchase a large amount of glutathione-glycine-$^{13}C_2$,$^{15}N$. Also, to synthesize glutathione-glycine-$^{13}C_2$,$^{15}N$, a very expensive glycine isotopologue is used as a raw material, and five steps are necessary to obtain glutathione-glycine-$^{13}C_2$,$^{15}N$. Therefore, it is very difficult to obtain glutathione-glycine-$^{13}C_2$,$^{15}N$ at low cost (Non Patent Literature 4) (Scheme 2).

Scheme 2

[Chemical Formula 11]

(SYNTHESIS METHOD IN THIS EMBODIMENT)

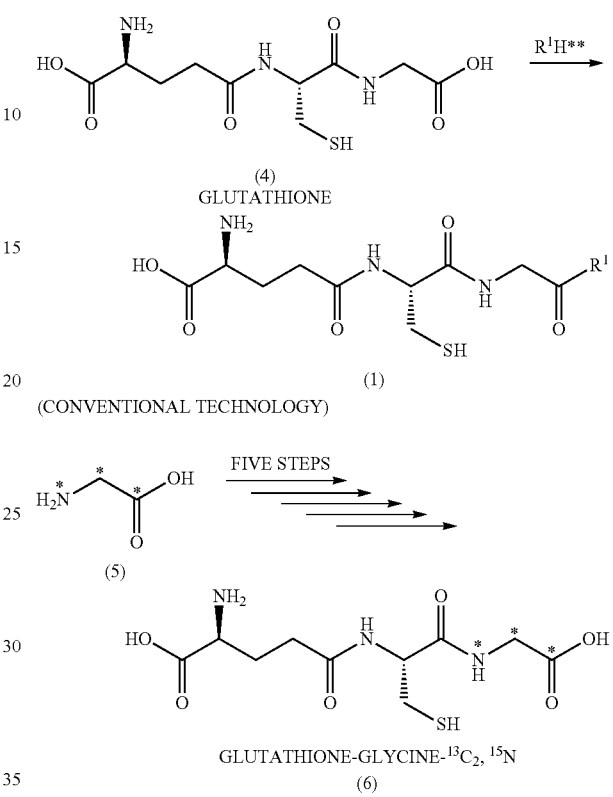

In Scheme 2, $R^1$ is as described above, and the hydrogen atom marked with two asterisks may also be substituted with an isotope.

According to this embodiment, a lower-cost isotope-labeled compound usable as a trapping agent can be provided. Therefore, an even more enormous number of drug candidate compounds can be screened. The capability of evaluating toxicity in a simple manner in the early stage of research and development may lead to speed-up of pharmaceutical drug development and has great significance.

In this embodiment, during incubation of the reaction sample containing the trapping agents (the substitution product represented by general formula (1) and the auxiliary detection compound) and the drug candidate compound, the trapping agents are reacted with a reactive metabolite to form trapping agent-reactive metabolite adducts. Therefore, ion peaks originating from the trapping agent-reactive metabolite adducts appear as a multiplet, i.e., for example, an auxiliary detection doublet, in LC-MS analysis etc. A multiplet such as an auxiliary detection doublet can be identified more easily than a single peak. Therefore, detection of a reactive metabolite can be performed with less false positive results.

The characteristic peak of an adduct of a reactive metabolite and the glutathione alkyl ester isotopologue according to this embodiment can facilitate the detection in LC-MS analysis by using a measurement method, such as a full scan method or a neutral loss scan method, in which ions can be detected continuously over a wide range. This allows detection with less false negative results.

In addition, when the substitution product of general formula (1) in this embodiment is used as a trapping agent, a reactive metabolite can be detected for a compound for which no reactive metabolite is detected using the conventional isotope-labeled compound as the trapping agent. Therefore, according to this embodiment, false negative results can be further reduced.

EXAMPLES

Example 1

Synthesis of Glutathione Ethyl Ester-d5 (Formula (3))

[Chemical Formula 12]

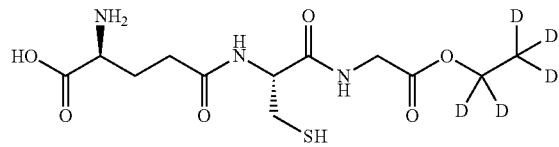

(3)

In formula (3), D represents deuterium ($^2$H).

Reduced glutathione (503.8 mg, 1.64 mmol) was suspended in ethanol-d6 (99.5 ATOM % D) (5 mL), and concentrated sulfuric acid (0.137 mL, 2.56 mmol) was added to the suspension to prepare a reaction mixture. The reaction mixture was stirred at room temperature for 30 minutes and left to stand at room temperature for 21 hours. Triethylamine (0.714 mL) was added to the reaction mixture for neutralization, and ethanol (10 mL) and diisopropyl ether (10 mL) were added to form a crystalline product. The reaction mixture was left to stand at 4° C. for 16 hours, and then the crystals were collected by filtration. The crystals were dried under reduced pressure at 35° C. for 3 hour to obtain 472 mg of a white solid (yield: 85%). ESI-MS (Positive) m/z 336 [M+H]$^+$ $^1$H-NMR (D2O, 400 MHz) δ: 1.98-2.04 (2H, m), 2.35-2.42 (2H, m), 2.79-2.81 (2H, m), 3.63 (1H, t, J=6.08 Hz), 3.87-3.88 (1H, m), 4.41 (1H, t, J=6.12 Hz)

Steps Common to Examples 2 to 9

Steps 1 and 2

(Step 1) In-Vitro Incubation and Analysis Sample Preparation

In the following Examples 2 to 9, a substrate compound that forms a reactive metabolite in a reactive metabolite detection test is referred to as an object compound.

An incubation mixture (reaction sample) containing an object compound (10 μmol/L, 10 nmol), a mixture (1 mmol/L, 1 μmol) obtained by mixing glutathione ethyl ester (GSHEE) and glutathione ethyl ester-d5 (GSHEE-d5) at a molar ratio of 1:1, rat liver microsomes (1 mg/mL, 1 mg), a potassium phosphate buffer (pH 7.4) (100 mmol/L, 100 μmol), magnesium chloride (5 mmol/L, 5 μmol), and purified water was pre-incubated at 37° C. for 5 minutes. NADPH (20 mmol/L, 20 μmol) was added to the pre-incubated incubation mixture and a reaction (incubation) was started. The final incubation volume was 1 mL. A sample containing no object compound was used as a control.

After incubation at 37° C. for 60 minutes, a 50 mmol/L aqueous dithiothreitol solution (100 μL, 5 μmol) was added to the incubation mixture, and the resultant mixture was subjected to centrifugation at 10,000 g for 5 minutes. The centrifugation supernatant was added to a solid phase extraction column (OASIS HLB 1 cc, 30 mg) that was pre-washed with 1 mL of methanol and activated with 1 mL of purified water. The column was washed with 1 mL of water and 1 mL of 5% methanol solution, and a reaction product was eluted with 1 mL of methanol. The solvent was removed by evaporation under nitrogen flow, and the residue was dissolved in 150 μL of acetonitrile:water (2:8) to prepare an analysis sample.

(Step 2) LC-MS Analysis
(Step 2-1) Liquid Chromatography

An AQCUITY UPLC system (WATERS) was used for separation by chromatography. Aliquots (10 μL) of the prepared analysis sample was injected into an AQCUITY UPLC BEH C18 column (2.1×100 mm, 1.7 μm). The separation by chromatography was performed under gradient conditions shown in the following table at a mobile phase flow rate of 0.5 mL/minute.

TABLE 1

| ANALYSIS TIME (MINUTES) | WATER CONTAINING 0.05% FORMIC ACID (%) | ACETONITRILE CONTAINING 0.05% FORMIC ACID (%) |
| --- | --- | --- |
| 0 | 90 | 10 |
| 1 | 90 | 10 |
| 6 | 60 | 40 |
| 8 | 10 | 90 |

(Step 2-2) Mass Analysis

The LC column eluate obtained in step 2-1 was introduced into an LTQ XL ion trap mass spectrometer. Ionization was performed in an ESI positive mode (a mode for detecting positively charged ions). The measurement conditions used are shown below (measurement conditions A).
(Measurement Conditions A)
ISplay Voltage: 5.0 kV
Capillary Temp: 350° C.
Sheath Gas Flow Rate: 41
Aux Gas Flow Rate: 18
Sweep Gas Flow Rate: 6.5

Figure 2:
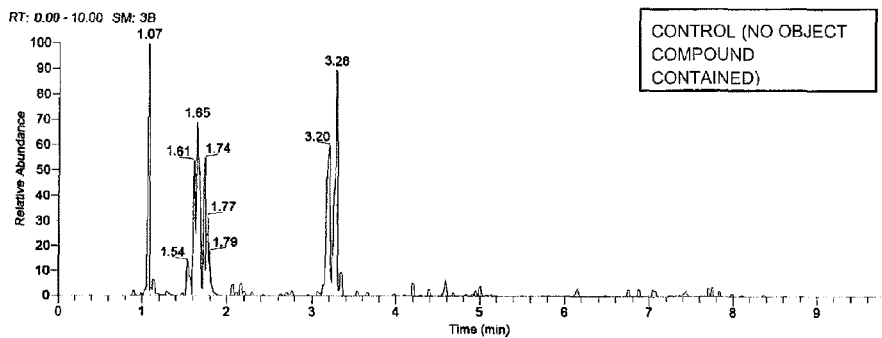
FIG. 2 is a final chromatogram when no object compound was used (control).
Figure 3:
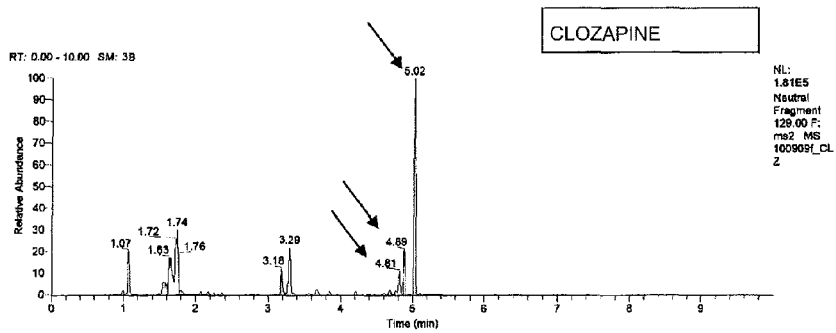
FIG. 3 is a final chromatogram when clozapine was used as the object compound.
Figure 5:
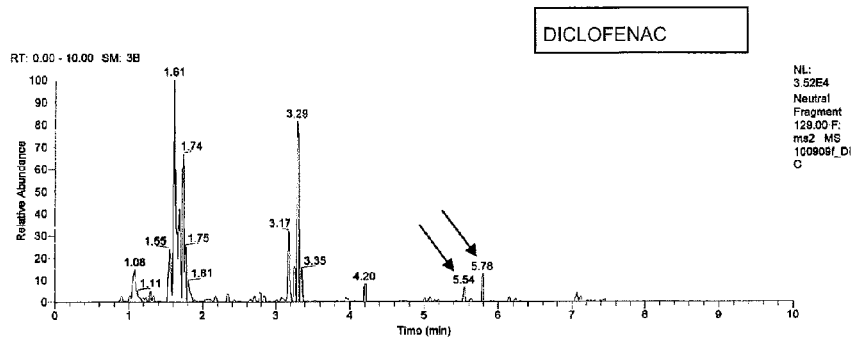
FIG. 5 is a final chromatogram when diclofenac was used as the object compound.
Figure 6:
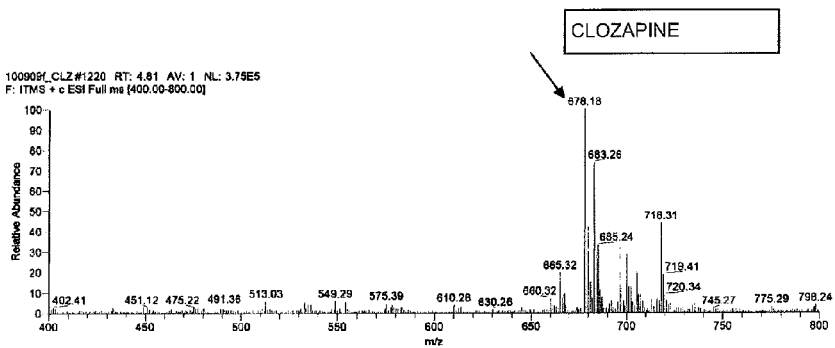
FIG. 6 is a first spectrum at a retention time of 4.81 minutes when clozapine was used as the object compound. The first spectrum includes peaks of adducts A.
Figure 7:
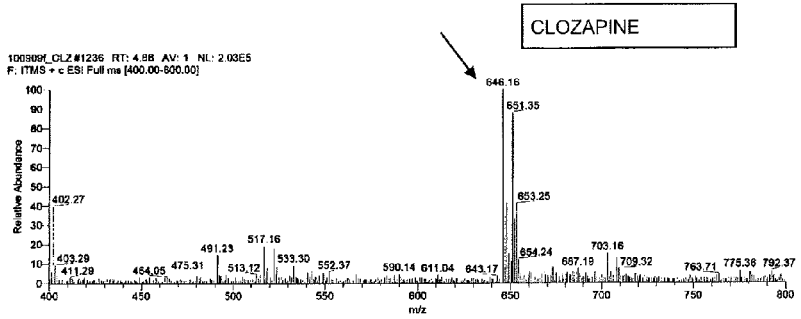
FIG. 7 is a first spectrum at a retention time of 4.89 minutes when clozapine was used as the object compound. The first spectrum includes peaks of adducts B.
Figure 8:
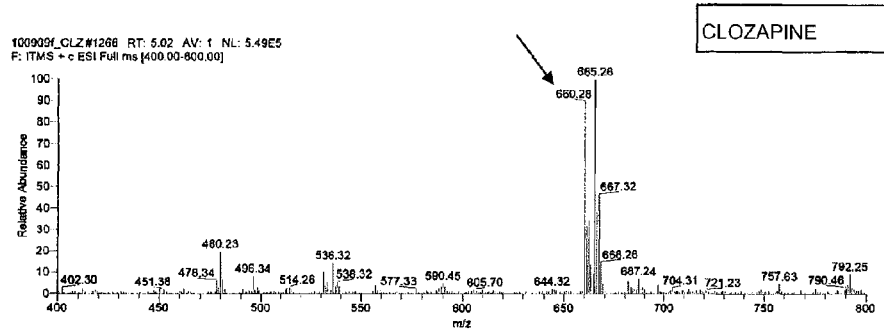
FIG. 8 is a first spectrum at a retention time of 5.02 minutes when clozapine was used as the object compound. The first spectrum includes peaks of adducts C.
Figure 9:
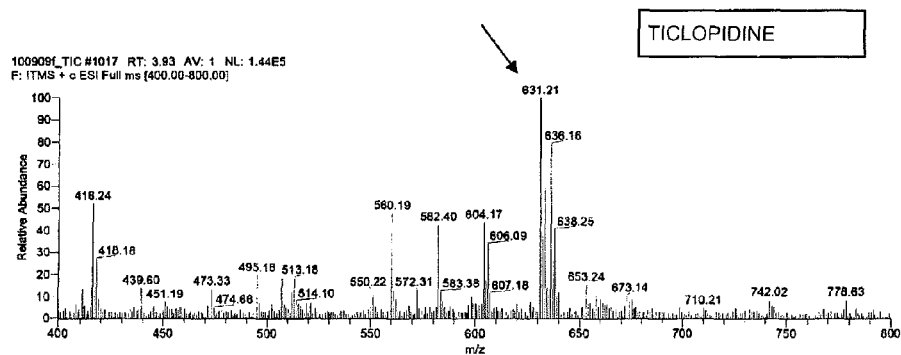
FIG. 9 is a first spectrum at a retention time of 3.92 minutes when ticlopidine was used as the object compound. The first spectrum includes peaks of adducts D.
Figure 10:
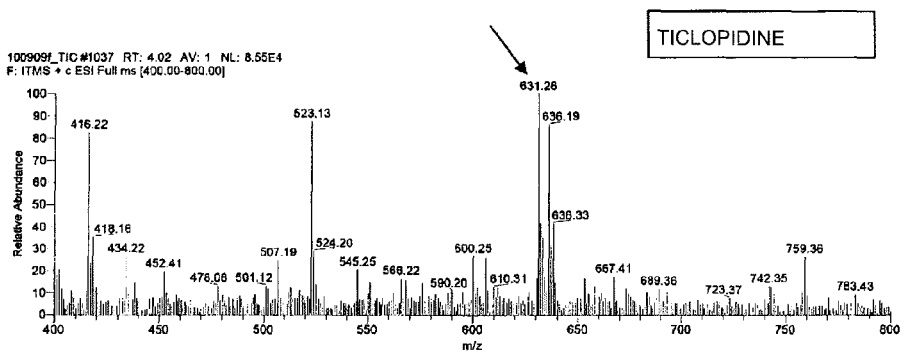
FIG. 10 is a first spectrum at a retention time of 4.02 minutes when ticlopidine was used as the object compound. The first spectrum includes peaks of adducts E.
Figure 11:
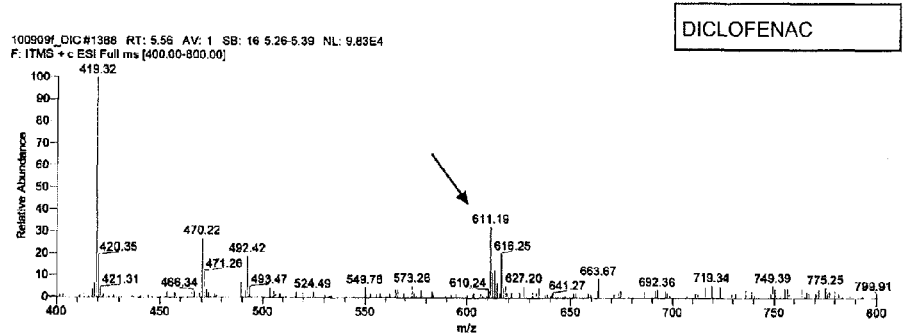
FIG. 11 is a first spectrum at a retention time of 5.56 minutes when diclofenac was used as the object compound. The first spectrum includes peaks of adducts F.
Figure 12:
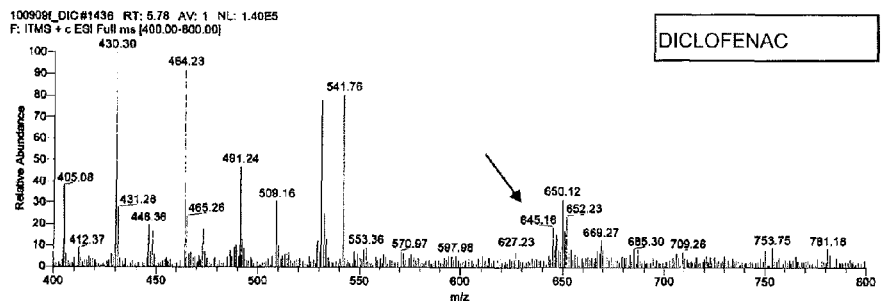
FIG. 12 is a first spectrum at a retention time of 5.78 minutes when diclofenac was used as the object compound. The first spectrum includes peaks of adducts G.
Figure 13:
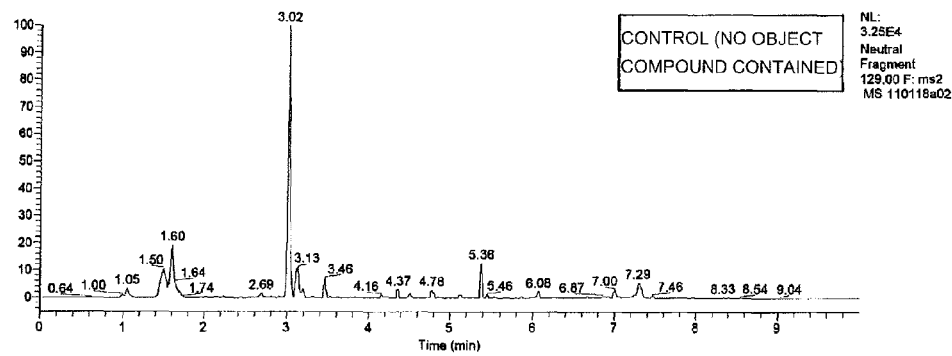
FIG. 13 is a final chromatogram when no object compound was used (control).
Figure 18:
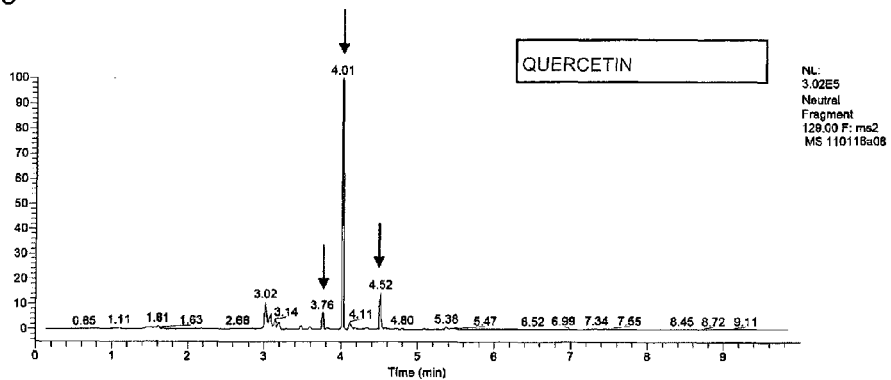
FIG. 18 is a final chromatogram when quercetin was used as the object compound.
Figure 19:
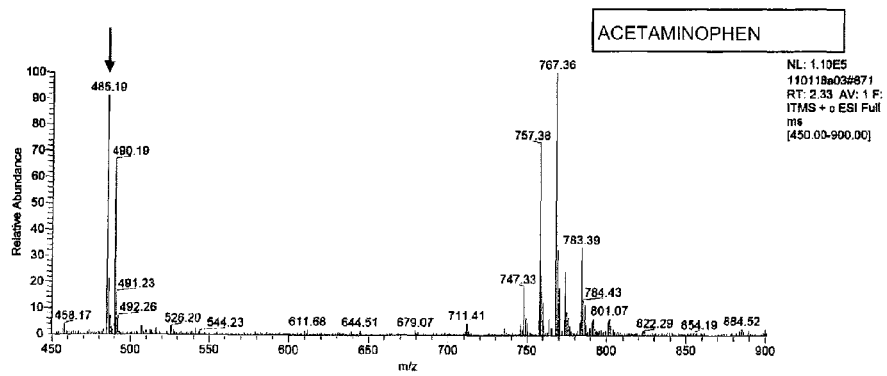
FIG. 19 is a first spectrum at a retention time of 2.33 minutes when acetaminophen was used as the object compound. The first spectrum includes peaks of adducts H.
Figure 20:
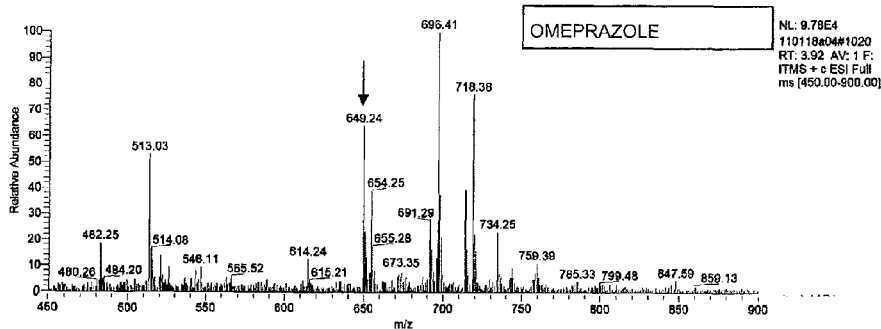
FIG. 20 is a first spectrum at a retention time of 3.92 minutes when omeprazole was used as the object compound. The first spectrum includes peaks of adducts I.
Figure 21:
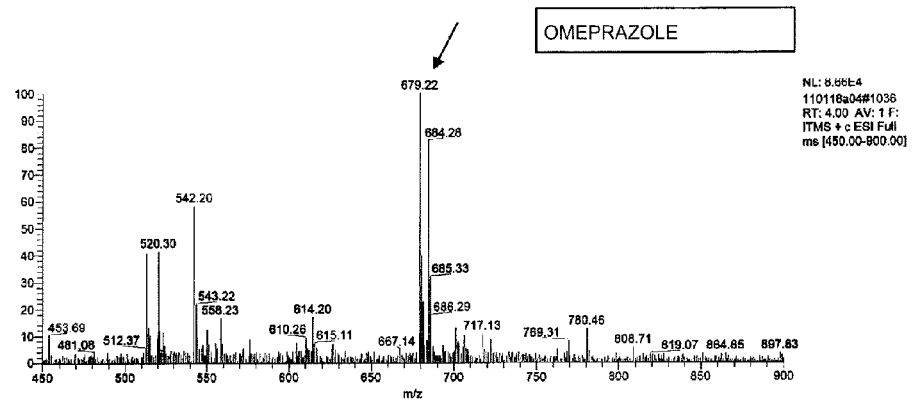
FIG. 21 is a first spectrum at a retention time of 3.99 minutes when omeprazole was used as the object compound. The first spectrum includes peaks of adducts J.
Figure 22:
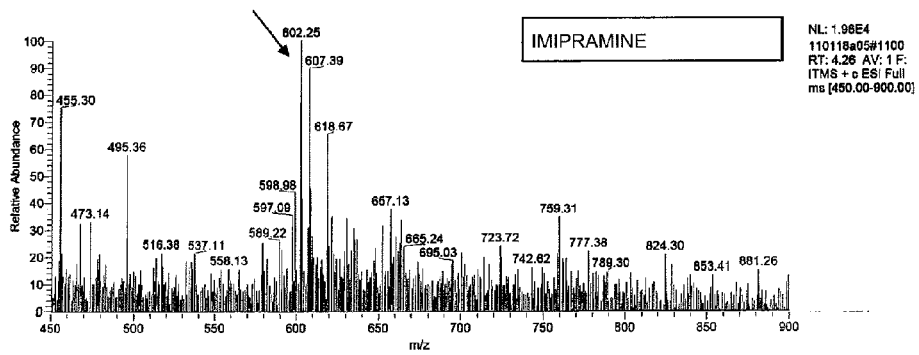
FIG. 22 is a first spectrum at a retention time of 4.27 minutes when imipramine was used as the object compound. The first spectrum includes peaks of adducts K.
Figure 23:
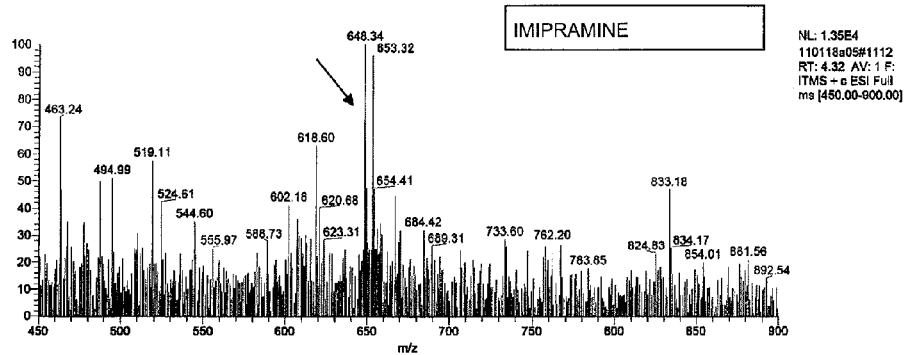
FIG. 23 is a first spectrum at a retention time of 4.33 minutes when imipramine was used as the object compound. The first spectrum includes peaks of adducts L.
Figure 24:
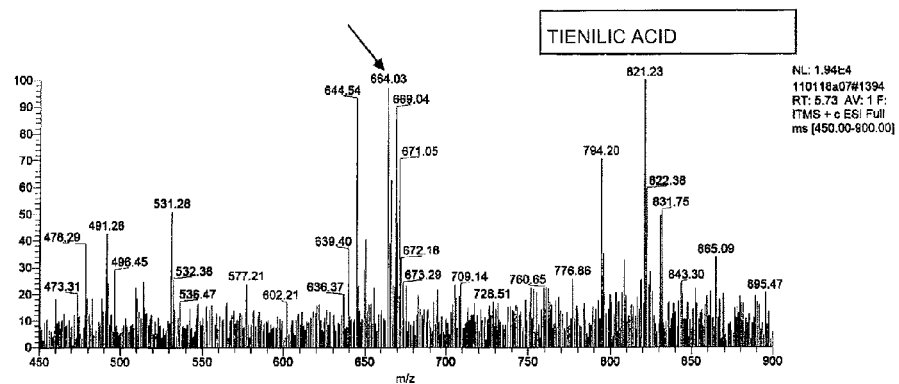
FIG. 24 is a first spectrum at a retention time of 5.74 minutes when tienilic acid was used as the object compound. The first spectrum includes peaks of adducts M.
Figure 25:
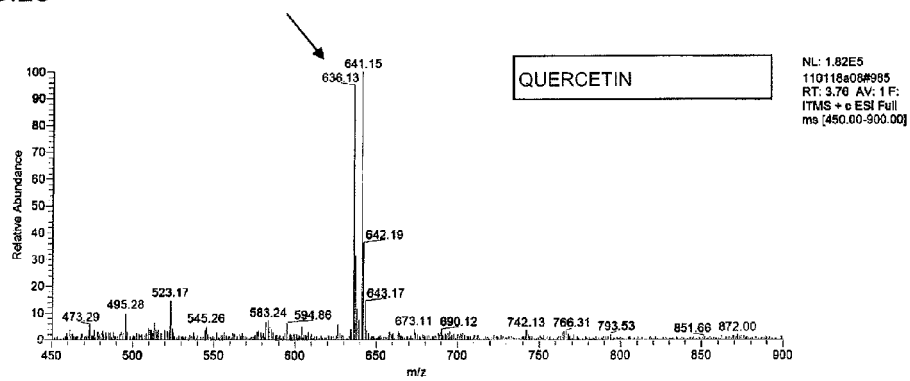
FIG. 25 is a first spectrum at a retention time of 3.76 minutes when quercetin was used as the object compound. The first spectrum includes peaks of adducts N.
Figure 26:
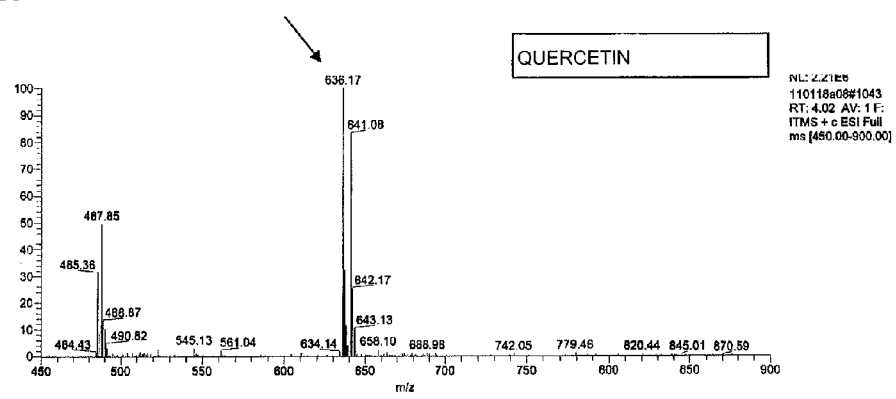
FIG. 26 is a first spectrum at a retention time of 4.01 minutes when quercetin was used as the object compound. The first spectrum includes peaks of adduct O.
Figure 27:
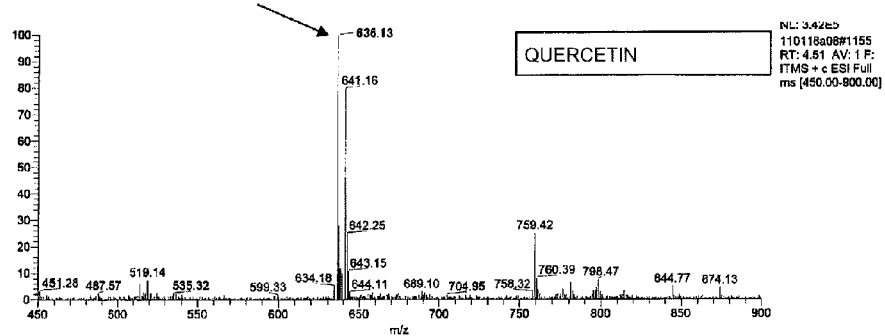
FIG. 27 is a first spectrum at a retention time of 4.52 minutes when quercetin was used as the object compound. The first spectrum includes peaks of adducts P.

Full scan measurement was performed over the mass-to-charge ratio (m/z) range of 400 to 800 to obtain a first chromatogram and first spectra shown in FIGS. 6 to 12 and 19 to 27 (clozapine: FIGS. 6 to 8, ticlopidine: FIGS. 9 and 10, diclofenac: FIGS. 11 and 12, acetaminophen: FIG. 19, omeprazole: FIGS. 20 and 21, imipramine: FIGS. 22 and 23, tienilic acid: FIG. 24, and quercetin: FIGS. 25 to 27).
(Step 2-3) MS/MS Measurement MS/MS measurement was performed in an isotopic data dependent scan mode in which only "ions with a difference of 5 amu and an intensity ratio of 1:1" which gave an isotopic doublet were subjected to collisional activation to thereby obtain a second spectrum. The measurement conditions used are shown below (measurement conditions B).
(Measurement Conditions B)
Normalized Collision Energy: 35
Mass Difference: 5.00
Expected ratio: 1.00
Match tolerance: 0.15
(Step 2-4) Neutral Loss Filter A 129 Da neutral loss filter was applied to the data set obtained by the MS/MS measurement in step 2-3 to acquire final chromatograms shown in FIGS. 2 to 5 and 13 to 18 (control: FIGS. 2 and 13, clozapine: FIG. 3, ticlopidine: FIG.

Figure 14:
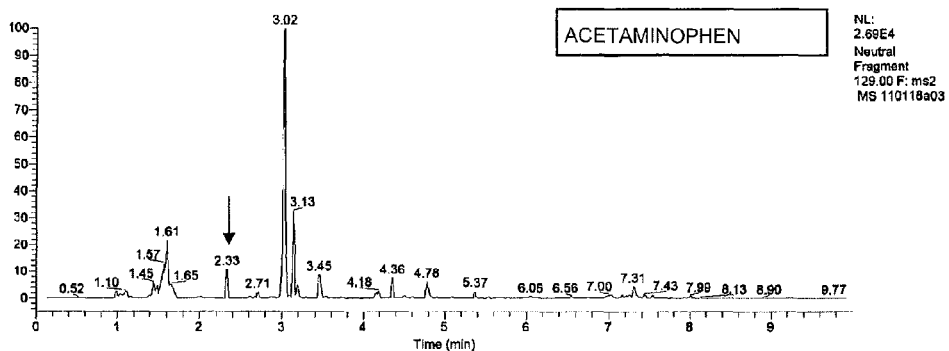
FIG. 14 is a final chromatogram when acetaminophen was used as the object compound.
Figure 15:
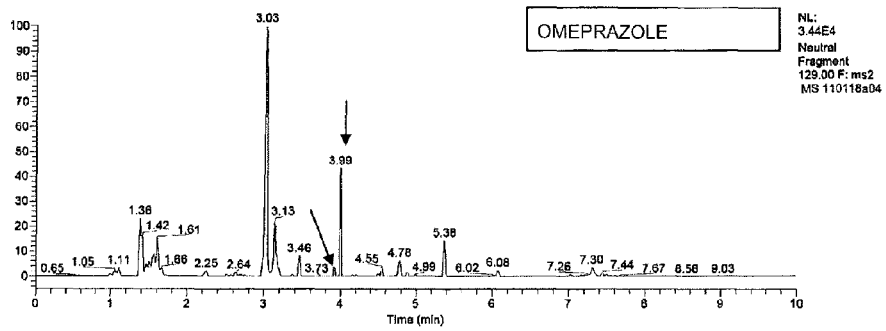
FIG. 15 is a final chromatogram when omeprazole was used as the object compound.
Figure 16:
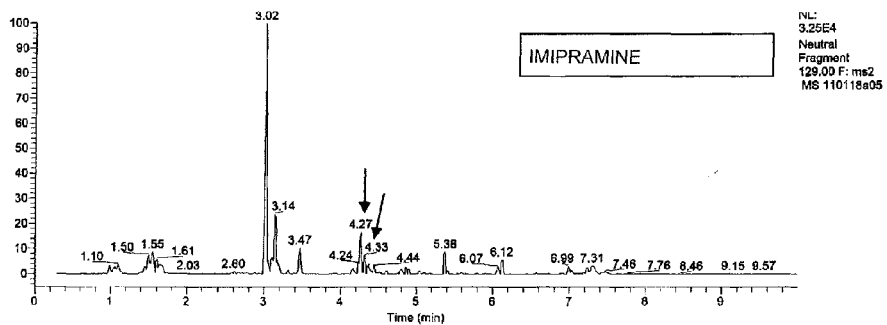
FIG. 16 is a final chromatogram when imipramine was used as the object compound.
Figure 17:
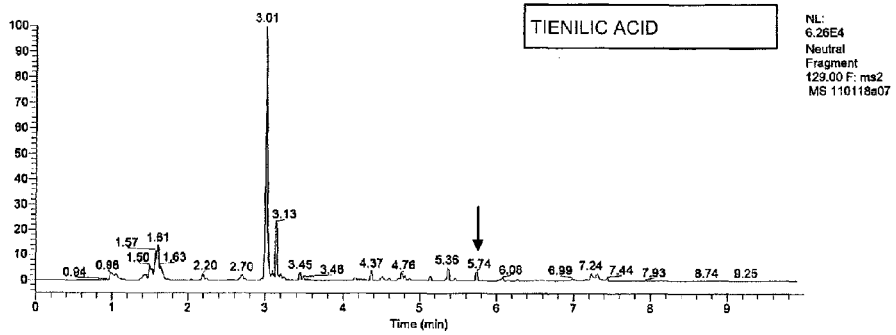
FIG. 17 is a final chromatogram when tienilic acid was used as the object compound.

4, diclofenac: FIG. 5, acetaminophen: FIG. 14, omeprazole: FIG. 15, imipramine: FIG. 16, tienilic acid: FIG. 17, and quercetin: FIG. 18).

The state of appearance of peaks in the chromatogram described above and the state of appearance of peaks in a mass analysis spectrum described later may vary according to the difference in lot of rat liver microsomes mixed with reaction samples and the difference in ionization state and sensitivity in the mass analyzer. Therefore, to perform more accurate analysis, a new control different from the control for Examples 1 to 4 (FIG. 2) was prepared for Examples 5 to 9, and measurement was performed for the new control (FIG. 13).

A final chromatogram shows peaks each corresponding to an isotopic doublet (a doublet with a difference of 5 amu and an intensity ratio of 1:1) in the mass analysis in step 2-2 and each showing a neutral loss of 129 Da detected in the second mass analysis (MS/MS measurement). Among the peaks appearing in the final chromatogram, peaks other than the peaks also appearing in the final chromatogram for the control (FIG. 2 or 13) are considered to be the peaks of trapping agent-reactive metabolite adducts.

The above measurement was performed using, as the object compound, each of clozapine, ticlopidine, diclofenac, acetaminophen, omeprazole, imipramine, tienilic acid, and quercetin. These eight compounds are known to form a reactive metabolite and were selected in order to verify whether glutathione ethyl ester-d5, one of the isotope-labeled compounds according to this embodiment, can be used to detect a reactive metabolite.

[Chemical Formula 13]

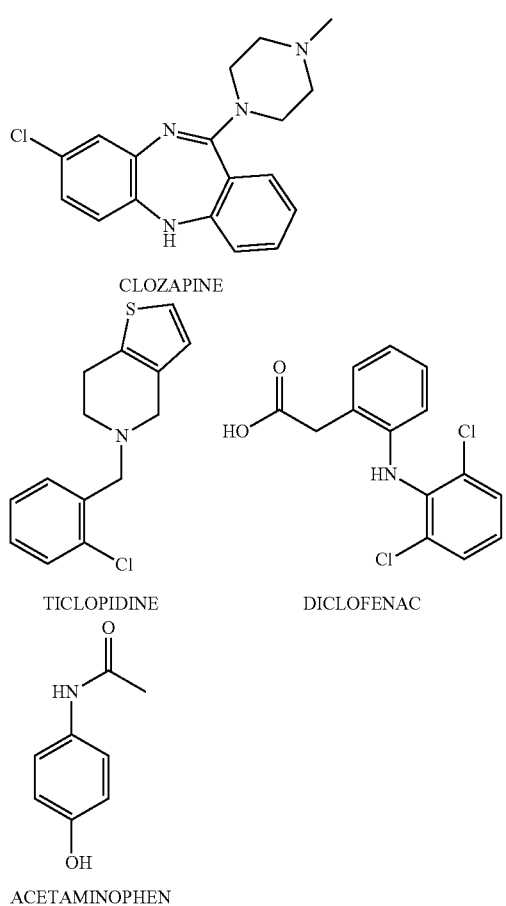

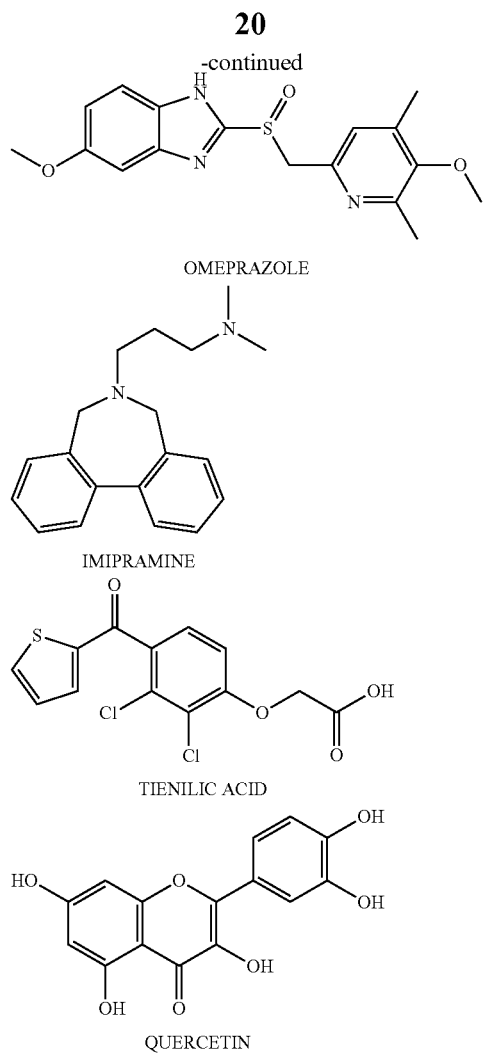

Example 2

Object Compound

Clozapine

FIG. 3 shows a final chromatogram obtained for the object compound. Several components showed positive responses. As compared with the chromatogram of the control (FIG. 2), peaks specific to the sample were recognized at retention times of 4.81 minutes, 4.89 minutes, and 5.02 minutes. Adducts corresponding to a retention time of 4.81 minutes are referred to as adducts A, adducts corresponding to a retention time of 4.89 minutes are referred to as adducts B, and adducts corresponding to a retention time of 5.02 minutes are referred to as adducts C. As shown in FIG. 6, a characteristic isotopic doublet was found at mass-to-charge ratios (m/z) of 678 and 683 Da for adducts A. As shown in FIG. 7, a characteristic isotopic doublet was found at mass-to-charge ratios (m/z) of 646 and 651 Da for adducts B. As shown in FIG. 8, a characteristic isotopic doublet was found at mass-to-charge ratios (m/z) of 660 and 665 Da for adducts C.

As can be seen from the above results, clozapine was judged positive even when glutathione ethyl ester-d5 was used as the trapping agent and found to form three types of reactive metabolites.

Example 3

Object Compound

Ticlopidine

Figure 4:
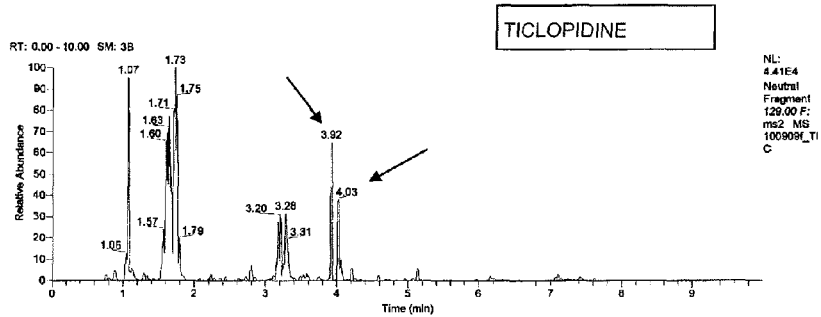
FIG. 4 is a final chromatogram when ticlopidine was used as the object compound.

FIG. 4 shows a final chromatogram obtained for the object compound. Several components showed positive responses. As compared with the chromatogram of the control (FIG. 2), peaks specific to the sample were recognized at retention times of 3.92 minutes and 4.03 minutes. Adducts corresponding to a retention time of 3.92 minutes are referred to as adducts D, and adducts corresponding to retention time of 4.03 minutes are referred to as adducts E. As shown in FIG. 9, a characteristic isotopic doublet was found at mass-to-charge ratios (m/z) of 631 and 636 Da for adducts D. As shown in FIG. 10, a characteristic isotopic doublet was found at mass-to-charge ratios (m/z) of 631 and 636 Da for adducts E.

As can be seen from the above results, ticlopidine was judged positive even when glutathione ethyl ester-d5 was used as the trapping agent and found to form two types of reactive metabolites.

Example 4

Object Compound

Diclofenac

FIG. 5 shows a final chromatogram obtained for the object compound. Several components showed positive responses. As compared with the chromatogram of the control (FIG. 2), peaks specific to the sample were recognized at retention times of 5.54 minutes and 5.78 minutes. Adducts corresponding to a retention time of 5.54 minutes are referred to as adducts F, and adducts corresponding to a retention time of 5.78 minutes are referred to as adducts G. As shown in FIG. 11, a characteristic isotopic doublet was found at mass-to-charge ratios (m/z) of 611 and 616 Da for adducts F. As shown in FIG. 12, a characteristic isotopic doublet was found at mass-to-charge ratios (m/z) of 645 and 650 Da for adducts G.

As can be seen from the above results, diclofenac was judged positive even when glutathione ethyl ester-d5 was used as the trapping agent and found to form two types of reactive metabolites.

Example 5

Object Compound

Acetaminophen

FIG. 14 shows a final chromatogram obtained for the object compound. Several components showed positive responses. As compared with the chromatogram of the control (FIG. 13), a peak specific to the sample was recognized at a retention time of 2.33 minutes. Adducts corresponding to a retention time of 2.33 minutes are referred to as adducts H. As shown in FIG. 19, a characteristic isotopic doublet was found at mass-to-charge ratios (m/z) of 485 and 490 Da for adducts H.

As can be seen from the above results, acetaminophen was judged positive even when glutathione ethyl ester-d5 was used as the trapping agent and found to form one type of reactive metabolite.

Example 6

Object Compound

Omeprazole

FIG. 15 shows a final chromatogram obtained for the object compound. Several components showed positive responses. As compared with the chromatogram of the control (FIG. 13), peaks specific to the sample were recognized at retention times of 3.92 minutes and 3.99 minutes. Adducts corresponding to a retention time of 3.92 minutes are referred to as adducts I, and adducts corresponding to a retention time of 3.99 minutes are referred to as adducts J. As shown in FIG. 20, a characteristic isotopic doublet was found at mass-to-charge ratios (m/z) of 649 and 654 Da for adducts I. As shown in FIG. 21, a characteristic isotopic doublet was found at mass-to-charge ratios (m/z) of 679 and 684 Da for adducts J.

As can be seen from the above results, omeprazole was judged positive even when glutathione ethyl ester-d5 was used as the trapping agent and found to form two types of reactive metabolites.

Example 7

Object Compound

Imipramine

FIG. 16 shows a final chromatogram obtained for the object compound. Several components showed positive responses. As compared with the chromatogram of the control (FIG. 13), peaks specific to the sample were recognized at retention times of 4.27 minutes and 4.33 minutes. Adduct corresponding to a retention time of 4.27 minutes are referred to as adducts K, and adducts corresponding to a retention time of 4.33 minutes are referred to as adducts L. As shown in FIG. 22, a characteristic isotopic doublet was found at mass-to-charge ratios (m/z) of 602 and 607 Da for adducts K. As shown in FIG. 23, a characteristic isotopic doublet was found at mass-to-charge ratios (m/z) of 648 and 653 Da for adducts L.

As can be seen from the above results, imipramine was judged positive even when glutathione ethyl ester-d5 was used as the trapping agent and found to form two types of reactive metabolites.

Example 8

Object Compound

Tienilic Acid

FIG. 17 shows a final chromatogram obtained for the object compound. Several components showed positive responses. As compared with the chromatogram of the control (FIG. 13), a peak specific to the sample was recognized at a retention time of 5.74 minutes. Adducts corresponding to a retention time of 5.74 minutes are referred to as adducts M. As shown in FIG. 24, a characteristic isotopic doublet was found at mass-to-charge ratios (m/z) of 664 and 669 Da for adducts M.

As can be seen from the above results, tienilic acid was judged positive even when glutathione ethyl ester-d5 was used as the trapping agent and found to form one type of reactive metabolite.

Example 9

Object Compound

Quercetin

FIG. 18 shows a final chromatogram obtained for the object compound. Several components showed positive responses. As compared with the chromatogram of the control (FIG. 13), peaks specific to the sample were recognized at retention times of 3.76 minutes, 4.01 minutes, and 4.52 minutes. Adducts corresponding to a retention time of 3.76 minutes are referred to as adducts N, adducts corresponding to a retention time of 4.01 minutes are referred to as adducts O, and adducts corresponding to a retention time of 4.52 minutes are referred to as adducts P. As shown in FIG. 25, a characteristic isotopic doublet was found at mass-to-charge ratios (m/z) of 636 and 641 Da for adducts N. As shown in FIG. 26, a characteristic isotopic doublet was found at mass-to-charge ratios (m/z) of 636 and 641 Da for adducts O. As shown in FIG. 27, a characteristic isotopic doublet was found at mass-to-charge ratios (m/z) of 636 and 641 Da for adducts P.

As can be seen from the above results, quercetin was judged positive even when glutathione ethyl ester-d5 was used as the trapping agent and found to form three types of reactive metabolites.

In Examples 2 to 9, glutathione ethyl ester-d5 represented by formula (3) was used as the trapping agent, and correct positive results were obtained for all the eight compounds (no false negative).

In Examples 2 to 9, peaks of glutathione alkyl ester isotopologue-reactive metabolite adducts and auxiliary detection compound-reactive metabolite adducts appeared as characteristic isotopic doublets. Therefore, the peaks of the glutathione alkyl ester isotopologue-reactive metabolite adducts and the auxiliary detection compound-reactive metabolite adducts can be easily distinguished from other peaks. Accordingly, the possibility of false positive results can be reduced.

Procedure Common to Comparative Examples 1 to 7

Glutathione ethyl ester (1 mmol/L, 1 μmol) was used as the trapping agent instead of the mixture of glutathione ethyl ester (GSHEE) and glutathione ethyl ester-d5 (GSHEE-d5), and the reaction and measurement were performed in the same manner as in (step 1) and (step 2) described above.

In the mass analysis corresponding to (step 2-2), full scan measurement was performed over the mass-to-charge ratio (m/z) range of 450 to 900. In the MS/MS measurement corresponding to (step 2-3), the MS/MS measurement was performed in a data dependent scan mode in which ions with the strongest intensity in a first spectrum were subjected to collisional activation to thereby obtain a second spectrum. The measurement conditions used are as follows (measurement conditions C).
(Measurement Conditions C)
Activation Type: CID
Normalized Collision Energy: 35

The above measurement was performed using, as the object compound, each of seven compounds, i.e., clozapine, diclofenac, acetaminophen, omeprazole, imipramine, tienilic acid, and quercetin. These seven compounds are known to form reactive metabolites and were selected in order to make comparisons with the results when the isotope-labeled compound according to this embodiment was used as the trapping agent to detect a reactive metabolite.

Figure 28:
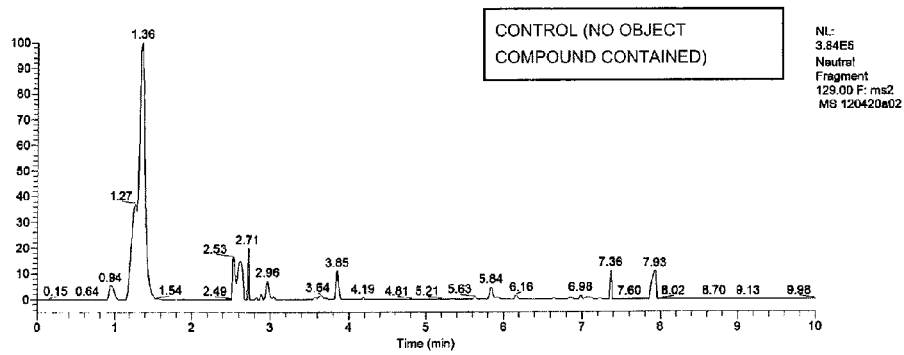
FIG. 28 is a final chromatogram when no object compounds were used in a Comparative Example (control).

A final spectrum obtained for a control is shown in FIG. 28.

Comparative Example 1

Object Compound

Omeprazole

Figure 29:
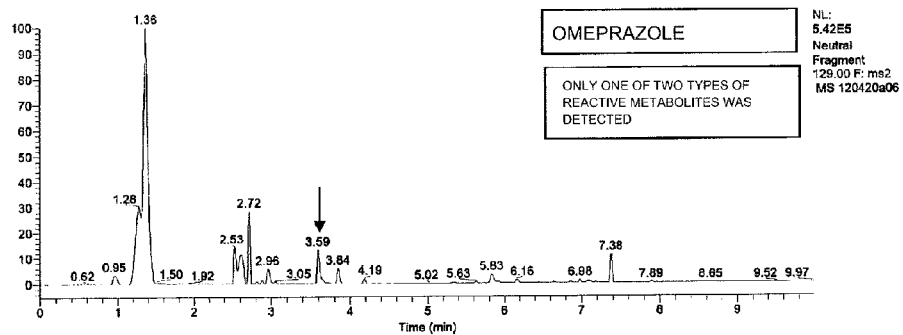
FIG. 29 is a final chromatogram when omeprazole was used as the object compound in a Comparative Example.
Figure 36:
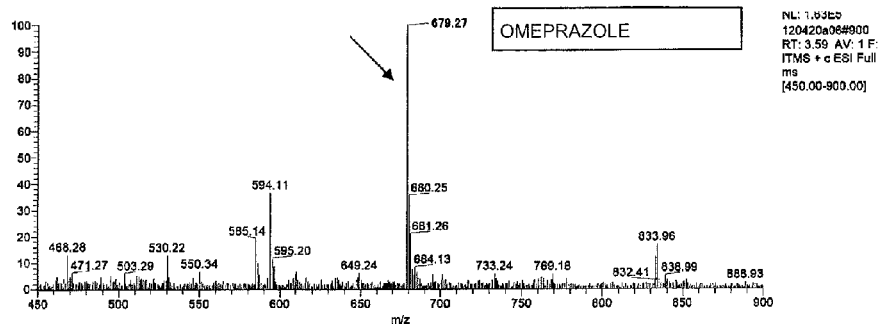
FIG. 36 is a first spectrum at a retention time of 3.59 minutes when omeprazole was used as the object compound in a Comparative Example. The first spectrum includes a peak of adduct Q.

FIG. 29 shows a final chromatogram obtained for the object compound. Several components showed positive responses. As compared with the chromatogram of the control (FIG. 28), a peak specific to the sample was recognized at a retention time of 3.59 minutes. An adduct corresponding to a retention time of 3.59 minutes is referred to as adduct Q. As shown in FIG. 36, a peak was found at a mass-to-charge ratio (m/z) of 679 Da for adduct Q.

Comparative Example 2

Object Compound

Clozapine

Figure 30:
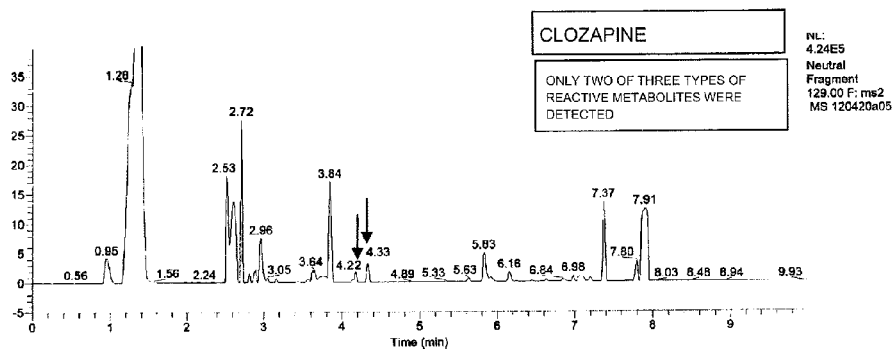
FIG. 30 is a final chromatogram when clozapine was used as the object compound in a Comparative Example.
Figure 37:
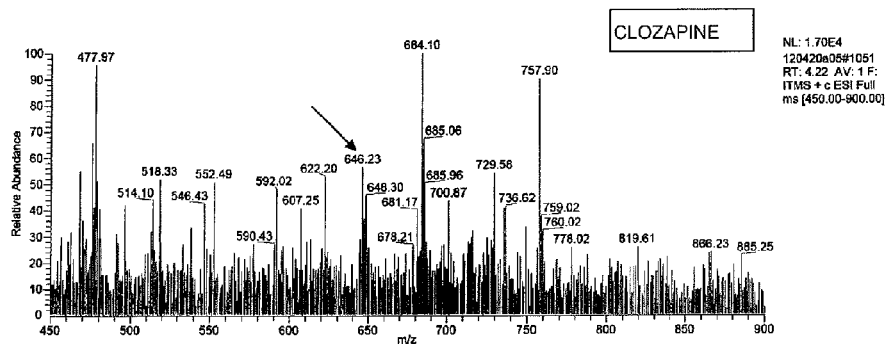
FIG. 37 is a first spectrum at a retention time of 4.22 minutes when clozapine was used as the object compound in a Comparative Example. The first spectrum includes a peak of adduct R.
Figure 38:
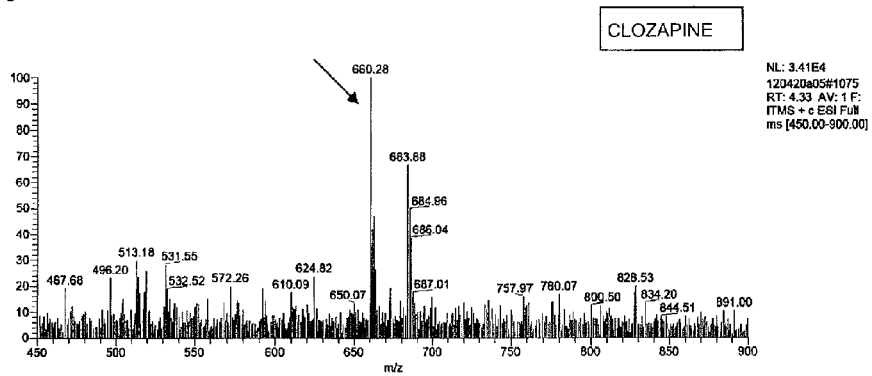
FIG. 38 is a first spectrum at a retention time of 4.33 minutes when clozapine was used as the object compound in a Comparative Example. The first spectrum includes a peak of adduct S.

FIG. 30 shows a final chromatogram obtained for the object compound. Several components showed positive responses. As compared with the chromatogram of the control (FIG. 28), peaks specific to the sample were recognized at retention times of 4.22 minutes and 4.33 minutes. An adduct corresponding to a retention time of 4.22 minutes is referred to as adduct R, and an adduct corresponding to a retention time of 4.33 minutes is referred to as adduct S. As shown in FIG. 37, a peak was found at a mass-to-charge ratio (m/z) of 646 Da for adduct R. As shown in FIG. 38, a peak was found at a mass-to-charge ratio (m/z) of 660 Da for adduct S.

Comparative Example 3

Object Compound

Diclofenac

Figure 31:
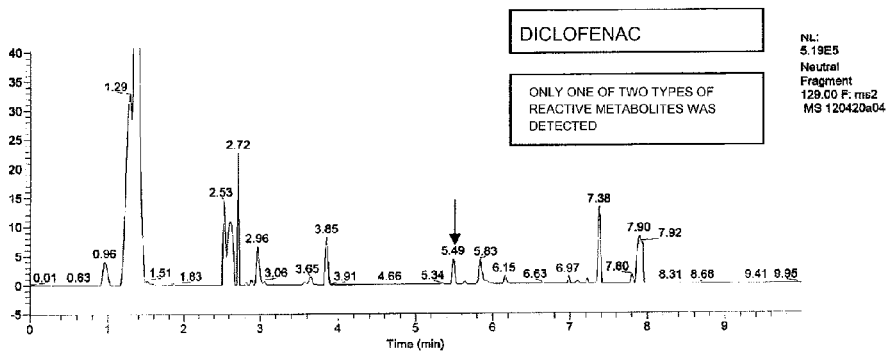
FIG. 31 is a final chromatogram when diclofenac was used as the object compound in a Comparative Example.
Figure 39:
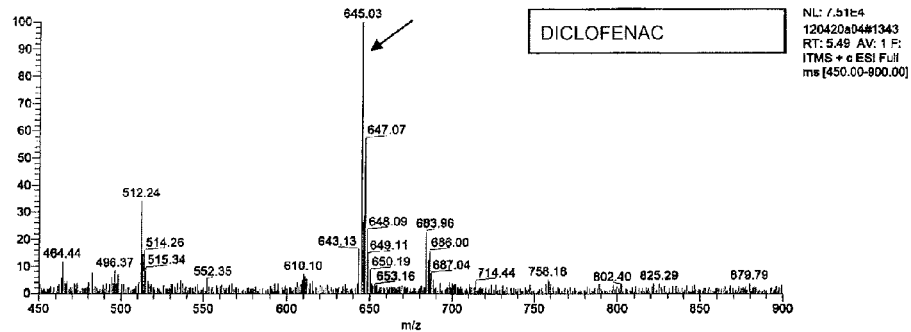
FIG. 39 is a first spectrum at a retention time of 5.49 minutes when diclofenac was used as the object compound in a Comparative Example. The first spectrum includes a peak of adduct T.

FIG. 31 shows a final chromatogram obtained for the object compound. Several components showed positive responses. As compared with the chromatogram of the control (FIG. 28), a peak specific to the sample was recognized at a retention time of 5.49 minutes. An adduct corresponding to a retention time of 5.49 minutes is referred to as adduct T. As shown in FIG. 39, a peak was found at a mass-to-charge ratio (m/z) of 645 Da for adduct T.

Comparative Example 4

Object Compound

Imipramine

Figure 32:
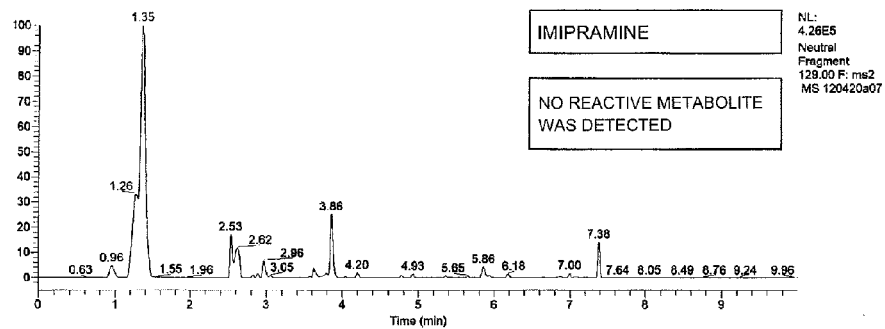
FIG. 32 is a final chromatogram when imipramine was used as the object compound in a Comparative Example.

FIG. 32 shows a final chromatogram obtained for the object compound. No peaks specific to the sample were found.

Comparative Example 5

Object Compound

Tienilic Acid

Figure 33:
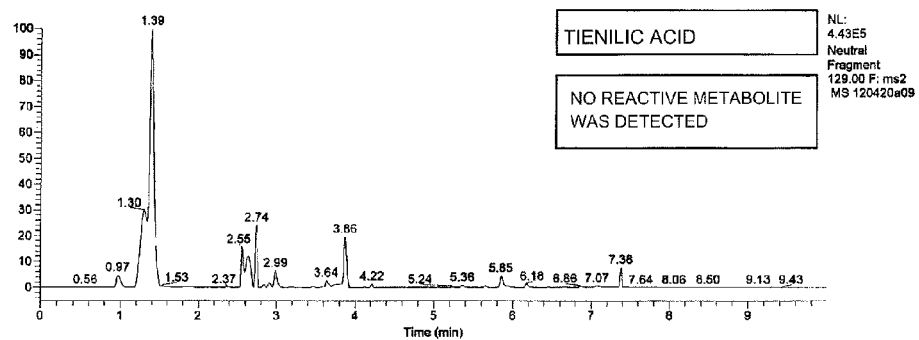
FIG. 33 is a final chromatogram when tienilic acid was used as the object compound in a Comparative Example.

FIG. 33 shows a final chromatogram obtained for the object compound. No peaks specific to the sample were found.

Comparative Example 6

Object Compound

Acetaminophen

Figure 34:
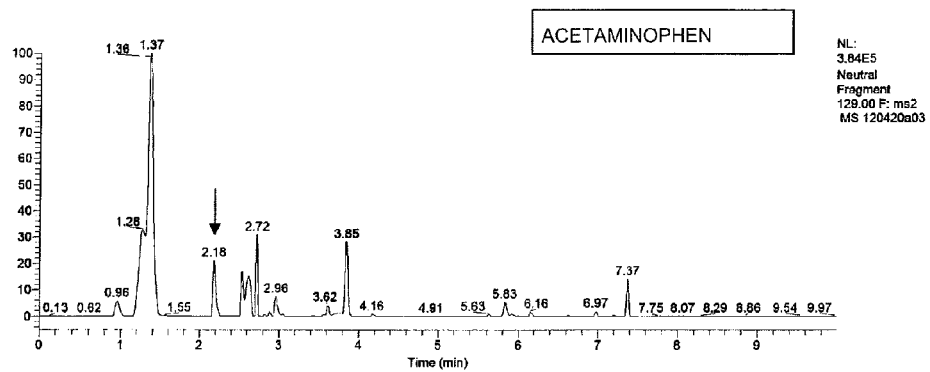
FIG. 34 is a final chromatogram when acetaminophen was used as the object compound in a Comparative Example.
Figure 40:
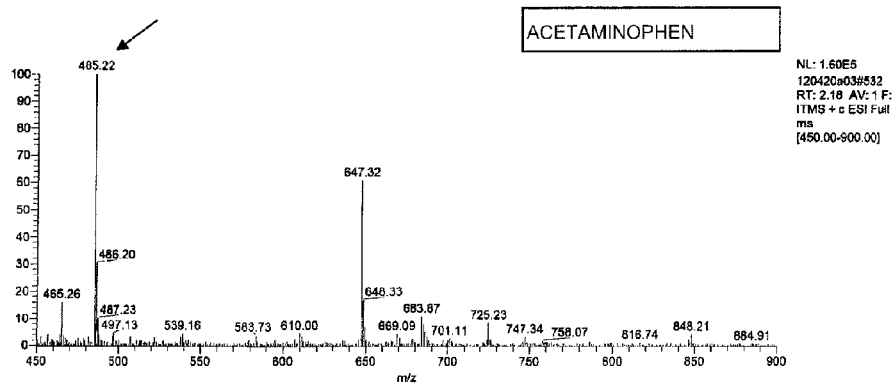
FIG. 40 is a first spectrum at a retention time of 2.18 minutes when acetaminophen was used as the object compound in a Comparative Example. The first spectrum includes a peak of adduct U.

FIG. 34 shows a final chromatogram obtained for the object compound. Several components showed positive responses. As compared with the chromatogram of the control (FIG. 28), a peak specific to the sample was recognized at a retention time of 2.18 minutes. An adduct corresponding to a retention time of 2.18 minutes is referred to as adduct U. As shown in FIG. 40, a peak was found at a mass-to-charge ratio (m/z) of 485 Da for adduct U.

Comparative Example 7

Object Compound

Quercetin

Figure 35:
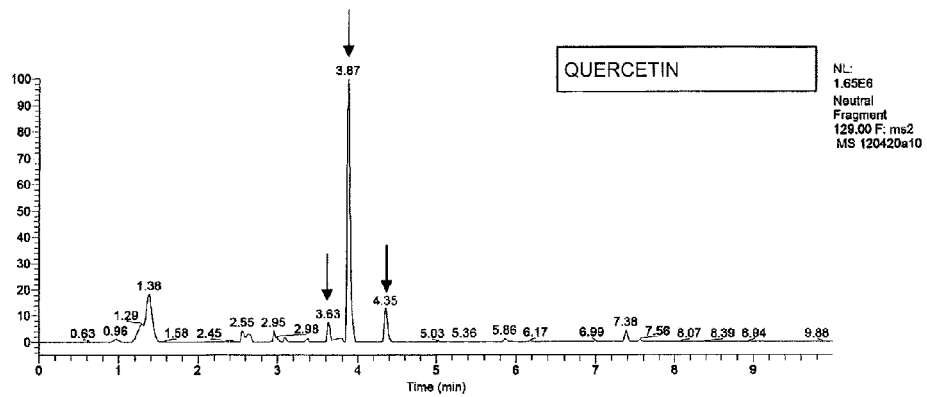
FIG. 35 is a final chromatogram when quercetin was used as the object compound in a Comparative Example.
Figure 41:
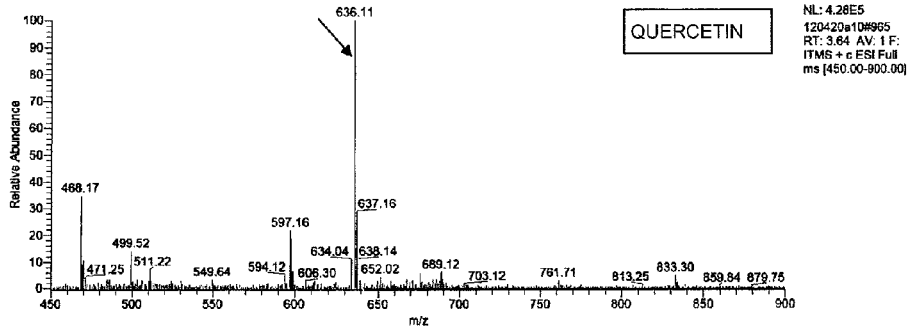
FIG. 41 is a first spectrum at a retention time of 3.63 minutes when quercetin was used as the object compound in a Comparative Example. The first spectrum includes a peak of adduct V.
Figure 42:
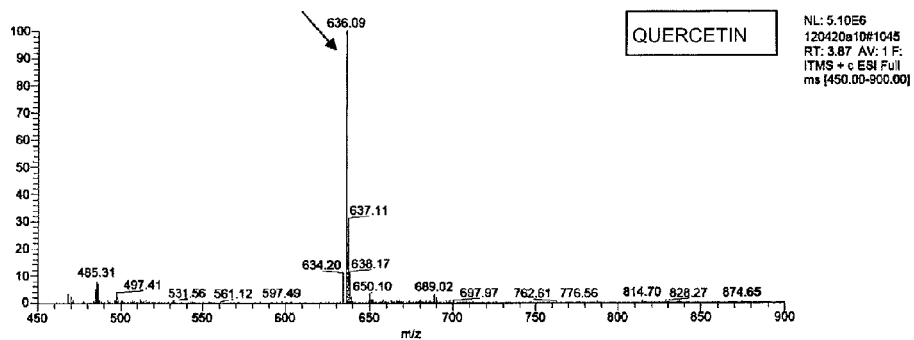
FIG. 42 is a first spectrum at a retention time of 3.87 minutes when quercetin was used as the object compound in a Comparative Example. The first spectrum includes a peak of adduct W.
Figure 43:
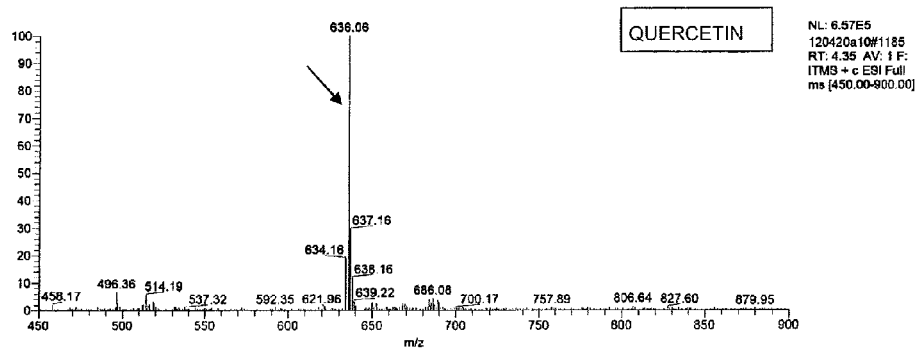
FIG. 43 is a first spectrum at a retention time of 4.35 minutes when quercetin was used as the object compound in a Comparative Example. The first spectrum includes a peak of adduct X.

FIG. 35 shows a final chromatogram obtained for the object compound. Several components showed positive responses. As compared with the chromatogram of the control (FIG. 28), peaks specific to the sample were recognized at retention times of 3.63 minutes, 3.87 minutes, and 4.35 minutes. An adduct corresponding to a retention time of 3.63 minutes is referred to as adduct V, an adduct corresponding to a retention time of 3.87 minutes is referred to as adduct W, and an adduct corresponding to a retention time of 4.35 minutes is referred to as adduct X. As shown in FIG. 41, a peak was found at a mass-to-charge ratio (m/z) of 636 Da for adduct V. As shown in FIG. 42, a peak was found at a mass-to-charge ratio (m/z) of 636 Da for adduct W. As shown in FIG. 43, a peak was found at a mass-to-charge ratio (m/z) of 636 Da for adduct X.

The results in the Examples and Comparative Examples 1 to 7 are shown in TABLE 2.

reactive metabolite adduct is low, this peak is not subjected to collisional activation. This may be the reason that the number of reactive metabolites identified was reduced.

As can be seen from the above results, with the isotope-labeled compound in this embodiment, false negative results are less likely to occur as compared with compounds conventionally used as the trapping agent. Therefore, the isotope-labeled compound is superior to the conventional compounds when used as the trapping agent.

The reason that the number of reactive metabolites identified was smaller in Comparative Examples 1 to 7 than in the Examples may be that "ions with the strongest intensity in a first spectrum were subjected to collisional activation" in the MS/MS measurement in (step 2-3). Therefore, further studies were performed under the conditions that collisional activation was performed for a trapping agent-reactive metabolite adduct even when its peak intensity was not strongest.

Comparative Example 8

Object Compound

Omeprazole

Omeprazole was used as the object compound. Measurement was performed in the same manner as in Comparative Example 1 except that the MS/MS measurement corresponding to (step 2-3) was performed in a data dependent scan

TABLE 2

|  | EXAMPLES | | COMPARATIVE EXAMPLES (GSHEE) | |
| --- | --- | --- | --- | --- |
|  | NUMBER OF IDENTIFIED REACTIVE METABOLITES | EXAMPLE NO. | NUMBER OF IDENTIFIED REACTIVE METABOLITES | COMPARATIVE EXAMPLE NO. |
| OMEPRAZOLE | 2 | EXAMPLE 6 | 1 | COMPARATIVE EXAMPLE 1 |
| CLOZAPINE | 3 | EXAMPLE 2 | 2 | COMPARATIVE EXAMPLE 2 |
| DICLOFENAC | 2 | EXAMPLE 4 | 1 | COMPARATIVE EXAMPLE 3 |
| IMIPRAMINE | 2 | EXAMPLE 7 | 0 | COMPARATIVE EXAMPLE 4 |
| TIENILIC ACID | 1 | EXAMPLE 8 | 0 | COMPARATIVE EXAMPLE 5 |
| ACETAMINOPHEN | 1 | EXAMPLE 5 | 1 | COMPARATIVE EXAMPLE 6 |
| QUERCETIN | 3 | EXAMPLE 9 | 3 | COMPARATIVE EXAMPLE 7 |

The cases in which the isotope-labeled compound in this embodiment was used as the trapping agent are compared with the cases in which only glutathione ethyl ester was used as the trapping agent. For five compounds (omeprazole, clozapine, diclofenac, imipramine, and tienilic acid) out of seven compounds, the number of reactive metabolites identified was larger in the Examples than in the Comparative Examples.

Particularly, for imipramine and tienilic acid, no reactive metabolite was detected in the Comparative Examples, and negative results were obtained. As described above, both of imipramine and tienilic acid are known as compounds that form a reactive metabolite, and therefore the above results are "false negative."

In the Examples in which the isotope-labeled compound in this embodiment was used as the trapping agent, the MS/MS measurement was performed with collisional activation being performed only for an isotopic doublet in each first spectrum.

However, in Comparative Examples 1 to 7, since glutathione ethyl ester was used, no isotopic doublet was observed. In Comparative Examples 1 to 7, ions with the strongest intensity were subjected to collisional activation. However, when the intensity of a peak of a trapping agent-mode (a Dynamic Exclusion ON mode) in which the MS/MS measurement was performed on ions in descending order of intensity. In the data dependent scan mode (Dynamic Exclusion ON mode), ions for a peak with the strongest intensity among the peaks in a first spectrum are subjected to MS/MS measurement three times. Then these ions are eliminated, and ions with the next strongest intensity are subjected to MS/MS measurement three times. This processing is repeated in order of intensity. The measurement conditions used are as follows (measurement conditions D).
(Measurement Conditions D)
Repeat Count: 3
Repeat Duration: 6.00
Exclusion List Size: 100
Exclusion Duration: 6.00

Figure 44:
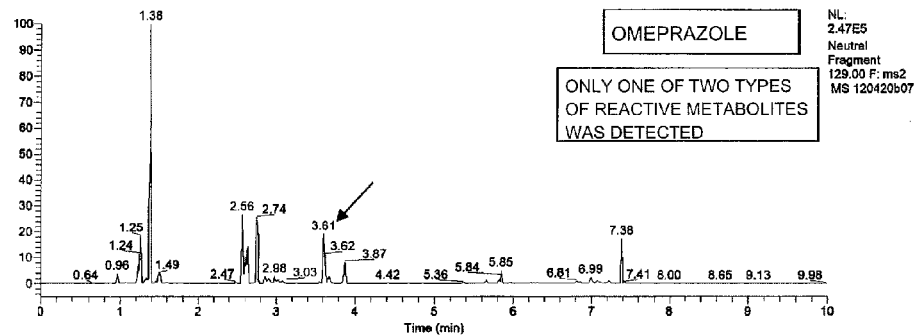
FIG. 44 is a final chromatogram when omeprazole was used as the object compound in a Comparative Example.
Figure 45:
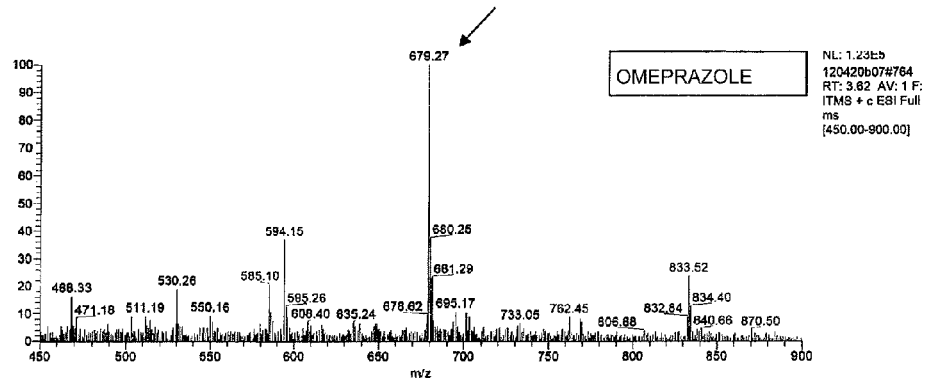
FIG. 45 is a first spectrum at a retention time of 3.61 minutes when omeprazole was used as the object compound in a Comparative Example. The first spectrum includes a peak of adduct Q2.

FIG. 44 shows a final chromatogram obtained for the object compound. Several components showed positive responses. As compared with the chromatogram of the control (FIG. 28), a peak specific to the sample was recognized at a retention time of 3.61 minutes. An adduct corresponding to a retention time of 3.61 minutes is referred to as adduct Q2. As shown in FIG. 45, a peak was found at a mass-to-charge ratio (m/z) of 679 Da for adduct Q2.

As can be seen from the above results, even when the conditions for the MS/MS measurement in (step 2-3) were changed, only one type of reactive metabolite was found, as in Comparative Example 1.

In Example 6, only an isotopic doublet among the peaks in each first spectrum can be subjected to collisional activation to perform MS/MS measurement, so that detection can be performed at high sensitivity. On the other hand, in Comparative Example 8, ions are activated sequentially in descending order of intensity. Therefore, when the intensity of the peak of a trapping agent-reactive metabolite adduct among the peaks in a first spectrum is low, the number of times of collisional activation becomes small. This may be the reason of the reduction in sensitivity.

As can be seen also from the above, with the isotope-labeled compound in this embodiment, false negative results are less likely to occur. Therefore, the isotope-labeled compound is superior when used as the trapping agent.

Procedure Common to Comparative Examples 9 to 15

(Step 1) In-Vitro Incubation and Analysis Sample Preparation

An incubation mixture (reaction sample) containing an object compound (10 μmol/L, 10 nmol), a mixture (1 mmol/L, 1 μmol) obtained by mixing glutathione (GSH) and glutathione-glycine-$^{13}C_2$,$^{15}N$ at a molar ratio of 1:0.7, rat liver microsomes (1 mg/mL, 1 mg), a potassium phosphate buffer (pH 7.4) (100 mmol/L, 100 μmol), magnesium chloride (5 mmol/L, 5 μmol), and purified water was pre-incubated at 37° C. for 5 minutes. NADPH (20 mmol/L, 20 μmol) was added to the pre-incubated incubation mixture and a reaction (incubation) was started. The final incubation volume was 1 mL. A sample containing no object compound was used as a control.

After incubation at 37° C. for 60 minutes, the resultant mixture was subjected to centrifugation at 10,000 g for 5 minutes. The centrifugation supernatant was added to a solid phase extraction column (OASIS HLB 1 cc, 30 mg) that was pre-washed with 1 mL of methanol and activated with 1 mL of purified water. The column was washed with 1 mL of water and 1 mL of 5% methanol water, and a reaction product was eluted with 1 mL of methanol. The solvent was removed by evaporation under nitrogen flow, and the residue was dissolved in 150 μL of acetonitrile:water (2:8) to prepare an analysis sample.

(Step 2) LC-MS Analysis
(Step 2-1) Liquid Chromatography

An AQCUITY UPLC system (WATERS) was used for separation by chromatography. Aliquots (10 μL) of the prepared analysis sample was injected into an AQCUITY UPLC BEH C18 column (2.1×100 mm, 1.7 μm). The separation by chromatography was performed under the gradient conditions shown in TABLE 3 at a mobile phase flow rate of 0.5 mL/minute.

TABLE 3

| ANALYSIS TIME (MINUTES) | WATER CONTAINING 0.05% FORMIC ACID (%) | ACETONITRILE CONTAINING 0.05% FORMIC ACID (%) |
| --- | --- | --- |
| 0 | 90 | 10 |
| 1 | 90 | 10 |
| 6 | 60 | 40 |
| 8 | 10 | 90 |

(Step 2-2) Mass Analysis

The LC column eluate obtained in step 2-1 was introduced into an LTQ XL ion trap mass spectrometer. Ionization was performed in an ESI positive mode (a mode for detecting positively charged ions). The measurement conditions used are shown below (measurement conditions A).

(Measurement Conditions A)
ISplay Voltage: 5.0 kV
Capillary Temp: 350° C.
Sheath Gas Flow Rate: 41
Aux Gas Flow Rate: 18
Sweep Gas Flow Rate: 6.5

Figure 53:
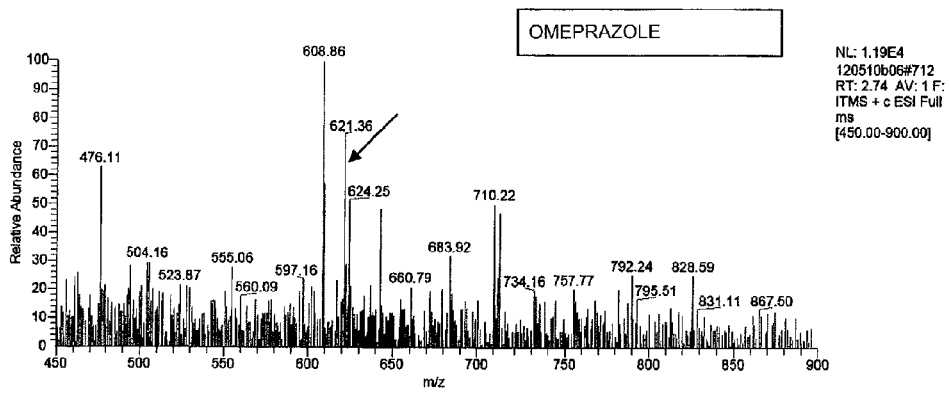
FIG. 53 is a first spectrum at a retention time of 2.74 minutes when omeprazole was used as the object compound in a Comparative Example. The first spectrum includes peaks of adducts Y.
Figure 54:
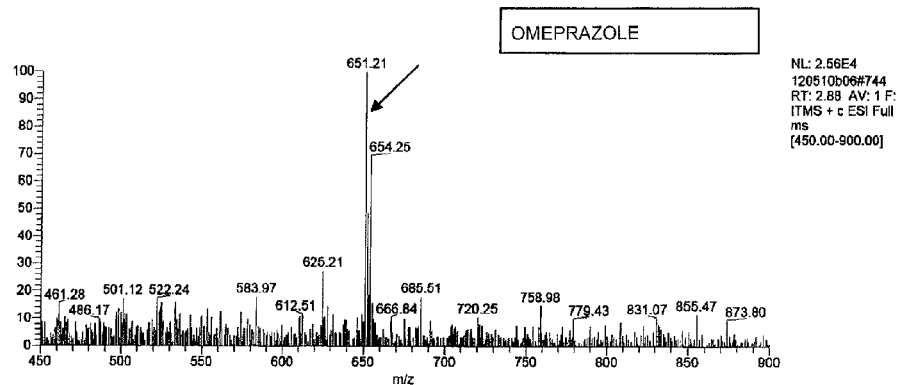
FIG. 54 is a first spectrum at a retention time of 2.88 minutes when omeprazole was used as the object compound in a Comparative Example. The first spectrum includes peaks of adducts Z.
Figure 55:
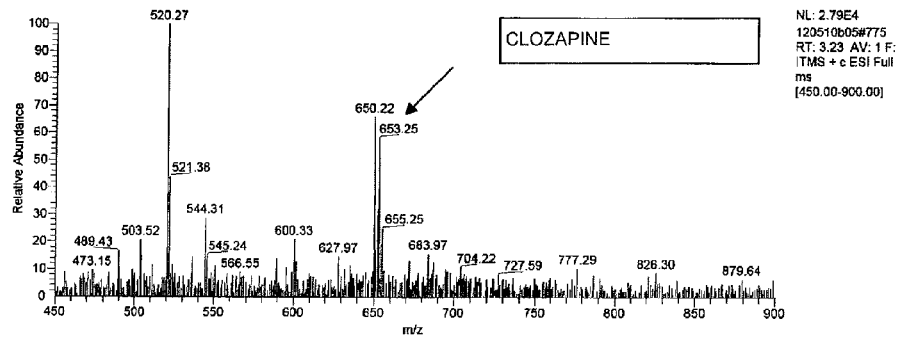
FIG. 55 is a first spectrum at a retention time of 3.22 minutes when clozapine was used as the object compound in a Comparative Example. The first spectrum includes peaks of adducts AA.
Figure 56:
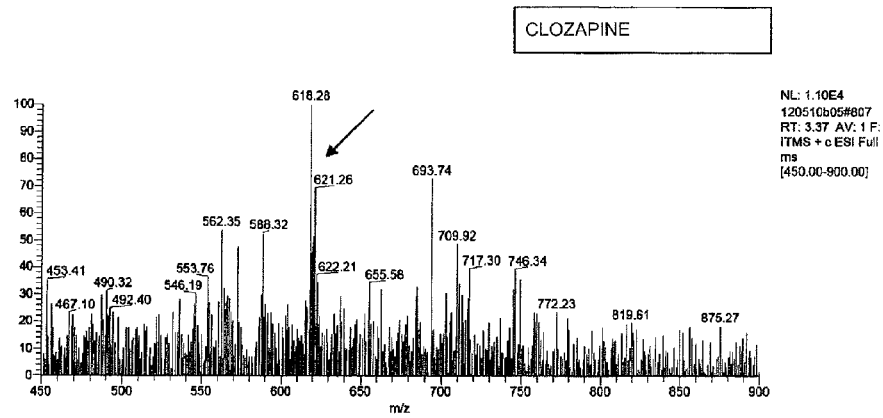
FIG. 56 is a first spectrum at a retention time of 3.37 minutes when clozapine was used as the object compound in a Comparative Example. The first spectrum includes peaks of adducts AB.
Figure 57:
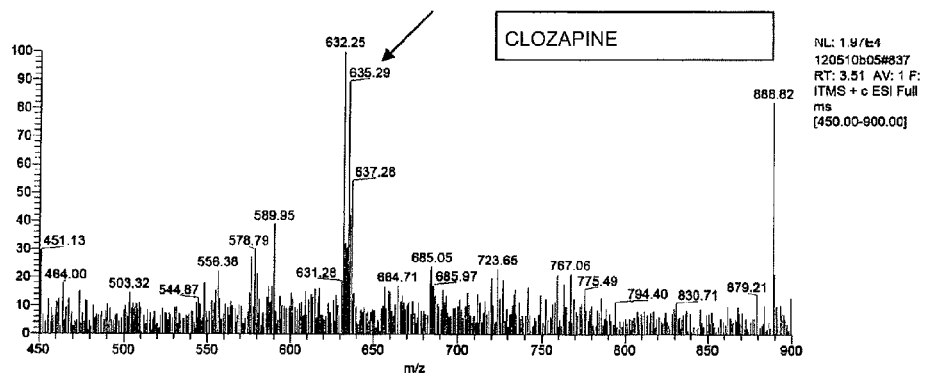
FIG. 57 is a first spectrum at a retention time of 3.50 minutes when clozapine was used as the object compound in a Comparative Example. The first spectrum includes peaks of adducts AC.
Figure 58:
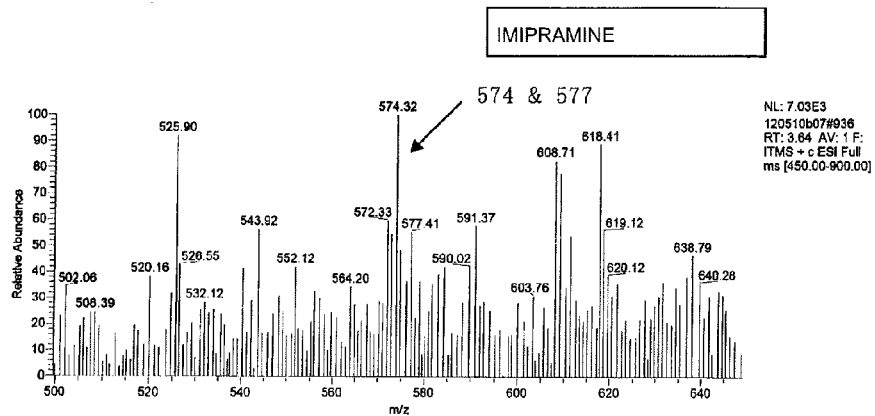
FIG. 58 is a first spectrum at a retention time of 3.65 minutes when imipramine was used as the object compound in a Comparative Example. The first spectrum includes peaks of adducts AD.
Figure 59:
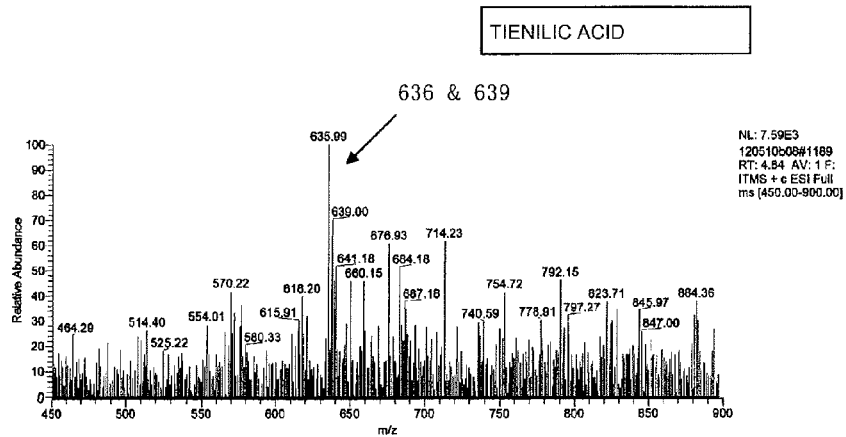
FIG. 59 is a first spectrum at a retention time of 4.85 minutes when tienilic acid was used as the object compound in a Comparative Example. The first spectrum includes peaks of adducts AE.
Figure 60:
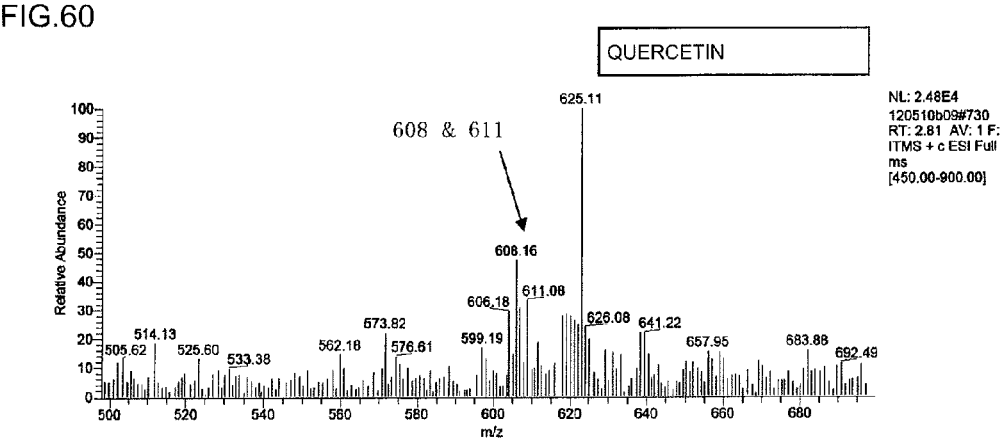
FIG. 60 is a first spectrum at a retention time of 2.82 minutes when quercetin was used as the object compound in a Comparative Example. The first spectrum includes peaks of adducts AF.
Figure 61:
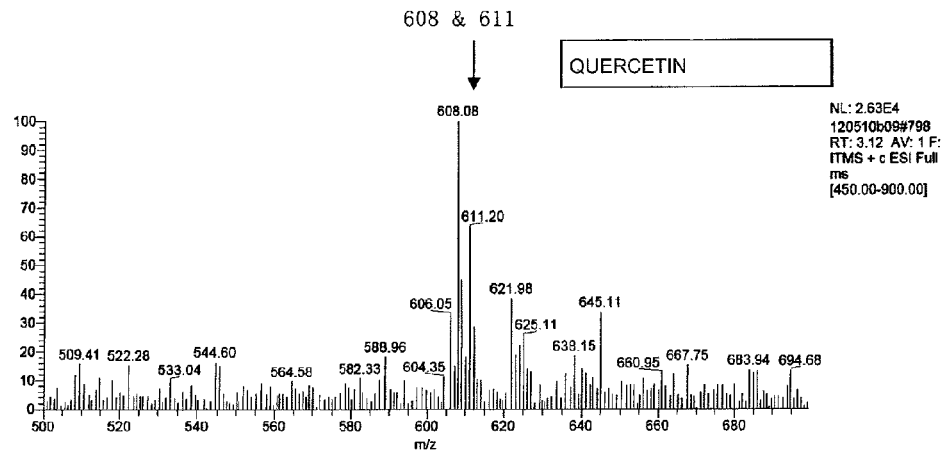
FIG. 61 is a first spectrum at a retention time of 3.16 minutes when quercetin was used as the object compound in a Comparative Example. The first spectrum includes peaks of adducts AG.

Full scan measurement was performed over the mass-to-charge ratio (m/z) range of 450 to 900 to obtain a first chromatogram and first spectra shown in FIGS. 53 to 61 (omeprazole: FIGS. 53 and 54, clozapine: FIGS. 55 to 57, imipramine: FIG. 58, tienilic acid: FIG. 59, and quercetin: FIGS. 60 and 61).

(Step 2-3) MS/MS Measurement

MS/MS measurement was performed in an isotopic data dependent scan mode in which only "ions with a difference of 3 amu and an intensity ratio of 1:0.7" which gave an isotopic doublet were subjected to collisional activation to thereby obtain a second spectrum. The measurement conditions used are shown below (measurement conditions E).

(Measurement Conditions E)
Normalized Collision Energy: 35
Mass Difference: 3.00
Expected ratio: 0.7
Match tolerance: 0.15

(Step 2-4) Neutral Loss Filter

Figure 46:
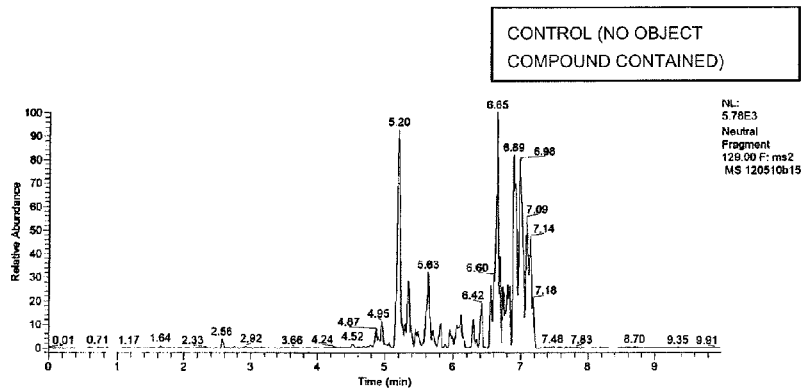
FIG. 46 is a final chromatogram when no object compounds were used in a Comparative Example (control).
Figure 47:
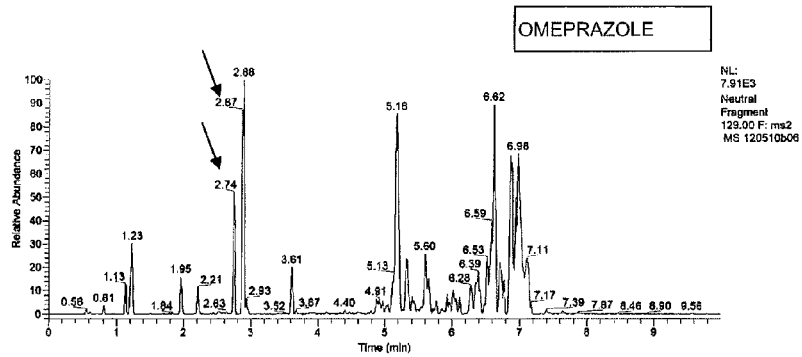
FIG. 47 is a final chromatogram when omeprazole was used as the object compound in a Comparative Example.
Figure 48:
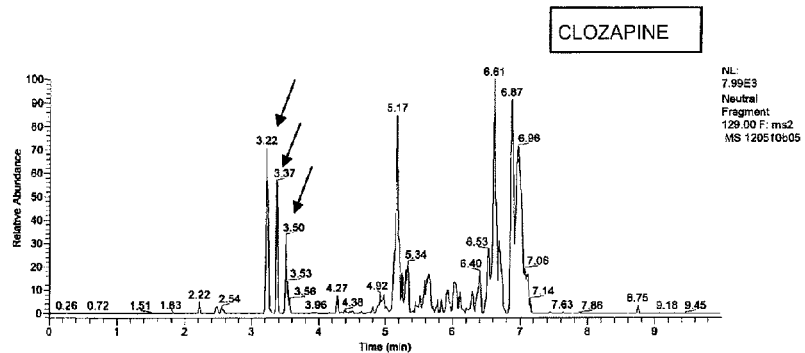
FIG. 48 is a final chromatogram when clozapine was used as the object compound in a Comparative Example.
Figure 49:
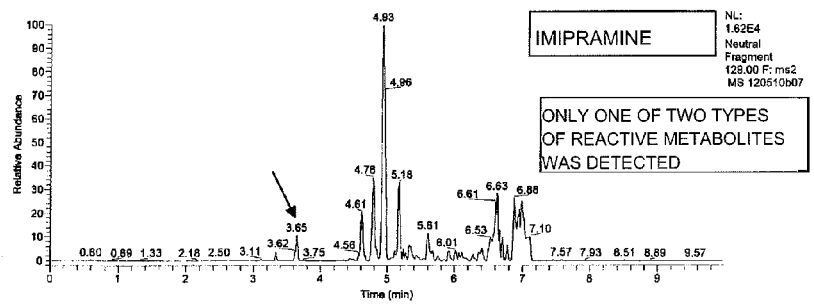
FIG. 49 is a final chromatogram when imipramine was used as the object compound in a Comparative Example.
Figure 50:
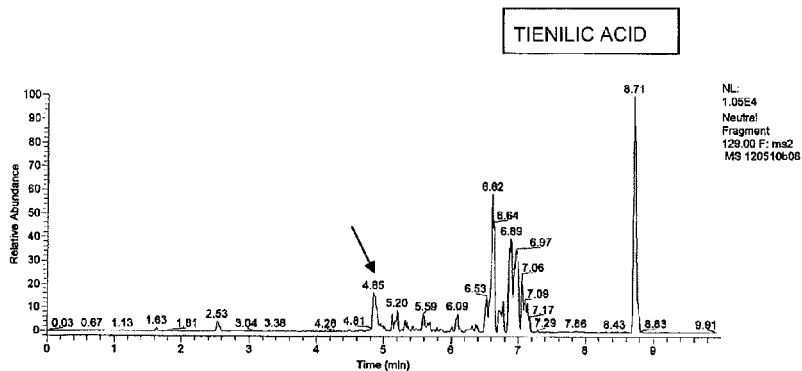
FIG. 50 is a final chromatogram when tienilic acid was used as the object compound in a Comparative Example.
Figure 51:
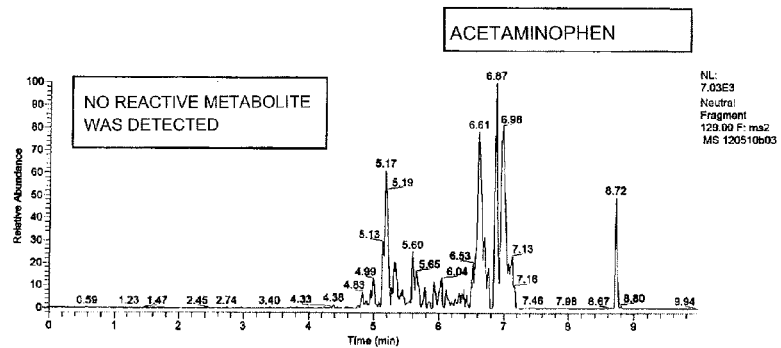
FIG. 51 is a final chromatogram when acetaminophen was used as the object compound in a Comparative Example.
Figure 52:
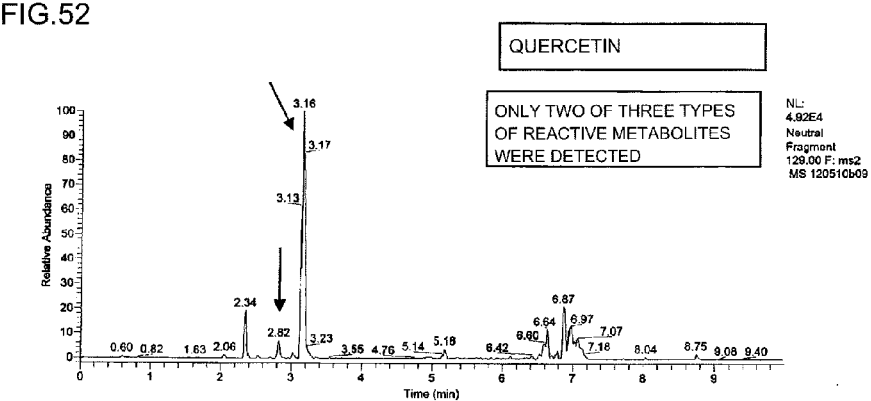
FIG. 52 is a final chromatogram when quercetin was used as the object compound in a Comparative Example.

A 129 Da neutral loss filter was applied to the data set obtained by the MS/MS measurement in step 2-3 to acquire final chromatograms shown in FIGS. 46 to 52 (control: FIG. 46, omeprazole: FIG. 47, clozapine: FIG. 48, imipramine: FIG. 49, tienilic acid: FIG. 50, acetaminophen: FIG. 51, and quercetin: FIG. 52).

A final chromatogram shows peaks each corresponding to an isotopic doublet (a doublet with a difference of 3 amu and an intensity ratio of 1:0.7) in the mass analysis in step 2-2 and each showing a neutral loss of 129 Da detected in the second mass analysis (MS/MS measurement). Among the peaks appearing in the final chromatogram, peaks other than the peaks also appearing in the final chromatogram for the control (FIG. 46) are considered to be the peaks of trapping agent-reactive metabolite adducts.

Comparative Example 9

Object Compound

Omeprazole

FIG. 47 shows a final chromatogram obtained for the object compound. Several components showed positive responses. As compared with the chromatogram of the control (FIG. 46), peaks specific to the sample were recognized at retention times of 1.13 minutes, 1.23 minutes, 1.95 minutes, 2.21 minutes, 2.74 minutes, 2.88 minutes, and 3.61 minutes. Of these, peaks at 1.13 minutes, 1.23 minutes, 1.95 minutes, 2.21 minutes, and 3.61 minutes are false positive peaks, and peaks at 2.74 minutes and 2.88 minutes are peaks of trapping agent-reactive metabolite adducts. Adducts corresponding to a retention time of 2.74 minutes are referred to as adducts Y. Adducts corresponding to a retention time of 2.88 minutes are referred to as adducts Z. As shown in FIG. 53, a characteristic isotopic doublet was found at mass-to-charge ratios (m/z) of 621 and 624 Da for adducts Y. As shown in FIG. 54, a characteristic isotopic doublet was found at mass-to-charge ratios (m/z) of 651 and 654 Da for adducts Z.

Comparative Example 10

Object Compound

Clozapine

FIG. 48 shows a final chromatogram obtained for the object compound. Several components showed positive responses. As compared with the chromatogram of the control (FIG. 46), peaks specific to the sample were recognized at retention times of 3.22 minutes, 3.37 minutes, and 3.50 minutes. Adducts corresponding to a retention time of 3.22 minutes are referred to as adducts AA, adducts corresponding to a retention time of 3.36 minutes are referred to as adducts AB, and adducts corresponding to a retention time of 3.50 minutes are referred to as adducts AC. As shown in FIG. 55, a characteristic isotopic doublet was found at mass-to-charge ratios (m/z) of 650 and 653 Da for adducts AA. As shown in FIG. 56, a characteristic isotopic doublet was found at mass-to-charge ratios (m/z) of 618 and 621 Da for adducts AB. As shown in FIG. 57, a characteristic isotopic doublet was found at mass-to-charge ratios (m/z) of 632 and 635 Da for adducts AC.

Comparative Example 11

Object Compound

Imipramine

FIG. 49 shows a final chromatogram obtained for the object compound. Several components showed positive responses. As compared with the chromatogram of the control (FIG. 46), peaks specific to the sample were recognized at retention times of 3.65 minutes, 4.61 minutes, 4.78 minutes, and 4.93 minutes. Of these, peaks at 4.61 minutes, 4.78 minutes, and 4.93 minutes are false positive peaks, and a peak at 3.65 minutes is the peak of a trapping agent-reactive metabolite adduct. Adducts corresponding to a retention time of 3.65 minutes are referred to as adducts AD. As shown in FIG. 58, a characteristic isotopic doublet was found at mass-to-charge ratios (m/z) of 574 and 577 Da for adducts AD.

Comparative Example 12

Object Compound

Tienilic Acid

FIG. 50 shows a final chromatogram obtained for the object compound. Several components showed positive responses. As compared with the chromatogram of the control (FIG. 46), peaks specific to the sample were recognized at retention times of 4.85 minutes and 8.71 minutes. Of these, a peak at 8.71 minutes is a false positive peak, and a peak at 4.85 minutes is the peak of a trapping agent-reactive metabolite adduct. Adducts corresponding to a retention time of 4.85 minutes are referred to as adducts AE. As shown in FIG. 59, a characteristic isotopic doublet was found at mass-to-charge ratios (m/z) of 636 and 639 Da for adducts AE.

Comparative Example 13

Object Compound

Acetaminophen

FIG. 51 shows a final chromatogram obtained for the object compound. No peaks of trapping agent-reactive metabolite adducts were found.

Comparative Example 14

Object Compound

Quercetin

FIG. 52 shows a final chromatogram obtained for the object compound. Several components showed positive responses. As compared with the chromatogram of the control (FIG. 46), peaks specific to the sample were recognized at retention times of 2.82 minutes and 3.16 minutes. Adducts corresponding to a retention time of 2.82 minutes are referred to as adducts AF, and adducts corresponding to a retention time of 3.16 minutes are referred to as adducts AG. As shown in FIG. 60, a characteristic isotopic doublet was found at mass-to-charge ratios (m/z) of 608 and 611 Da for adducts AF. As shown in FIG. 61, a characteristic isotopic doublet was found at mass-to-charge ratios (m/z) of 608 and 611 Da for adducts AG.

The results for Examples and Comparative Examples are shown in TABLE 4.

TABLE 4

| | EXAMPLES | | COMPARATIVE EXAMPLES ([13C2, 15N]GSH | |
|---|---|---|---|---|
| | NUMBER OF IDENTIFIED REACTIVE METABOLITES | EXAMPLE NO. | NUMBER OF IDENTIFIED REACTIVE METABOLITES | COMPARATIVE EXAMPLE NO. |
| OMEPRAZOLE | 2 | EXAMPLE 6 | 2 | COMPARATIVE EXAMPLE 9 |
| CLOZAPINE | 3 | EXAMPLE 2 | 3 | COMPARATIVE EXAMPLE 10 |
| IMIPRAMINE | 2 | EXAMPLE 7 | 1 | COMPARATIVE EXAMPLE 11 |
| TIENILIC ACID | 1 | EXAMPLE 8 | 1 | COMPARATIVE EXAMPLE 12 |
| ACETAMINOPHEN | 1 | EXAMPLE 5 | 0 | COMPARATIVE EXAMPLE 13 |
| QUERCETIN | 3 | EXAMPLE 9 | 2 | COMPARATIVE EXAMPLE 14 |

The cases in which the isotope-labeled compound in this embodiment was used as the trapping agent are compared with the cases in which glutathione-glycine-$^{13}C_2,^{15}N$ was used. For three compounds (imipramine, acetaminophen, and quercetin) out of six compounds, the number of reactive metabolites identified was larger in the Examples than in the Comparative Examples. Particularly, for acetaminophen, no reactive metabolite was detected in the Comparative Example, and negative results were obtained. As described above, acetaminophen is known as a compound that forms a reactive metabolite, and therefore the above results are "false negative."

When glutathione-glycine-$^{13}C_2,^{15}N$ was used for omeprazole (Comparative Example 9), imipramine (Comparative Example 11), and tienilic acid (Comparative Example 12), false positive peaks that were not found when the isotope-labeled compound in this embodiment was used were found.

As can be seen from the above results, with the isotope-labeled compound in this embodiment, false negative results and false positive results are less likely to occur as compared with compounds conventionally used as the trapping agent. Therefore, the isotope-labeled compound is superior to the conventional compounds when used as the trapping agent.

INDUSTRIAL APPLICABILITY

A novel isotope-labeled compound that can be used as a trapping agent useful to select a drug candidate compound that forms a reactive metabolite is provided. In addition, a detection method and a detection agent that result in not only less false positive results but also less false negative results and can detect a reactive metabolite more correctly are provided.

The invention claimed is:

1. A glutathione alkyl ester isotopologue represented by general formula 3:

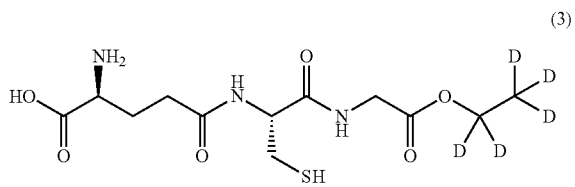

(3)

wherein D represents deuterium ($^2$H).

2. A method for detecting a reactive metabolite using the glutathione alkyl ester isotopologue according to claim 1, the method comprising:

incubating a reaction sample containing the glutathione alkyl ester isotopologue, an auxiliary detection compound which is a compound obtained by substituting at least one atom contained in the glutathione alkyl ester isotopologue with an atom having a mass number different from a mass number of the at least one atom, and a drug candidate compound in the presence of a drug metabolizing enzyme thereby forming a product containing a glutathione alkyl ester isotopologue-reactive metabolite adduct and an auxiliary detection compound-reactive metabolite adduct; and detecting a mass peak of the formed glutathione alkyl ester isotopologue-reactive metabolite adduct and a mass peak of the formed auxiliary detection compound-reactive metabolite adduct through analysis using a liquid chromatography-mass spectrometer (LC-MS).

3. The method for detecting a reactive metabolite according to claim 2, wherein a molar ratio of the glutathione alkyl ester isotopologue to the auxiliary detection compound in the reaction sample is 2:1 to 1:2.

4. The method for detecting a reactive metabolite according to claim 2, the method further comprising:

adding dithiothreitol, 2-mercaptoethanol, or tris(2-carboxyethyl)phosphine to the product obtained by incubation; and then performing the analysis using the liquid chromatography-mass spectrometer (LC-MS).

5. The method for detecting a reactive metabolite according to claim 2, wherein a neutral loss scan method or a full scan method is performed in the analysis using the liquid chromatography-mass spectrometer (LC-MS).

6. The method for detecting a reactive metabolite according to claim 2, wherein the auxiliary detection compound is a non-labeled compound of the glutathione alkyl ester isotopologue contained in the reaction sample.

7. A method for producing the glutathione alkyl ester isotopologue according to claim 1, comprising reacting glutathione with ethanol-d6.

* * * * *